United States Patent [19]
Arakawa

[11] Patent Number: 5,233,193
[45] Date of Patent: Aug. 3, 1993

[54] RADIATION IMAGE RECORDING APPARATUS

[75] Inventor: Satoshi Arakawa, Kanagawa, Japan

[73] Assignee: Fuji Photo Film Co., Ltd., Kanagawa, Japan

[21] Appl. No.: 815,185

[22] Filed: Dec. 31, 1991

[30] Foreign Application Priority Data

Jan. 10, 1991 [JP] Japan .................................. 3-001404
Jan. 10, 1991 [JP] Japan .................................. 3-001405
Jan. 11, 1991 [JP] Japan .................................. 3-002263

[51] Int. Cl.$^5$ .......................................... G01N 23/04
[52] U.S. Cl. ................................. 250/327.2; 378/155; 378/146
[58] Field of Search ................... 250/327.2, 484.1; 378/154, 155, 150, 153, 146, 147

[56] References Cited

U.S. PATENT DOCUMENTS

| | | | |
|---|---|---|---|
| 1,874,577 | 8/1932 | Morrison | 378/154 |
| 2,139,098 | 12/1938 | Raney | 378/155 |
| 4,096,391 | 6/1978 | Barnes | 378/155 |
| 4,258,264 | 3/1981 | Kotera et al. | 250/489.1 |
| 4,651,002 | 3/1987 | Anno | 378/155 |
| 4,864,134 | 9/1989 | Hosoi et al. | 250/327.2 |
| 5,065,022 | 11/1991 | Horikawa | 250/327.2 |

FOREIGN PATENT DOCUMENTS

56-11395 2/1981 Japan .
59-85650 5/1984 Japan .
60-149043 8/1985 Japan .

Primary Examiner—Drew A. Dunn
Attorney, Agent, or Firm—Sughrue, Mion, Zinn, Macpeak & Seas

[57] ABSTRACT

A radiation image recording apparatus comprises a source of radiation and a radiation image recording medium located facing the radiation source. A first slit plate is composed of a radiation absorber and at least two parallel slits, through which the radiation passes. The first slit plate is located between the radiation source and an object, which object is placed between the radiation source and the radiation image recording medium. A second slit plate is composed of a radiation absorber and at least two parallel slits, through which the radiation passes. The second slit plate is located between the object and the radiation image recording medium such that the slits of the second slit plate may be parallel to the slits of the first slit plate. A drive device synchronously moves the first slit plate and the second slit plate in the direction, along which the slits stand side by side with each other, such that a plane, which passes through one of the slits of the first slit plate and one of the slits of the second slit plate, may pass through the radiation source. At least either one of the first slit plate and the second slit plate has a cross-sectional shape such that the thicknesses of walls, which extend on both sides of each slit and define each slit, may become progressively smaller towards each slit.

25 Claims, 16 Drawing Sheets

RADIATION IMAGE RECORDING APPARATUS

BACKGROUND OF THE INVENTION

1. Field of the Invention

This invention relates to a radiation image recording apparatus wherein a radiation image recording medium is exposed to radiation, which has passed through an object, and a radiation image of the object is thereby recorded on the radiation image recording medium. This invention particularly relates to a radiation image recording apparatus, which is of the slit exposure type and in which adverse effects of radiation scattered by an object are eliminated.

2. Description of the Prior Art

Radiation image recording apparatuses have heretofore been used wherein a sheet of X-ray photographic film intervening between two fluorescent intensifying screens is exposed to radiation, which has passed through an object, and a radiation image of the object is thereby recorded on the X-ray photographic film. Radiation image recording apparatuses have heretofore been used wherein a fluorescent plate is exposed to radiation, which has passed through an object, the fluorescence being thereby produced by the fluorescent plate, and the fluorescence is photoelectrically detected by an image intensifier, or the like, whereby an electric signal representing a radiation image of the object is obtained.

When certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor.

As disclosed in U.S. Pat. No. 4,258,264 and Japanese Unexamined Patent Publication No. 56(1981)-11395, it has been proposed to use stimulable phosphors in obtaining electric signals representing radiation images of objects. Specifically, a sheet provided with a layer of the stimulable phosphor (hereinafter referred to as a stimulable phosphor sheet) is first exposed to radiation which has passed through an object, such as the human body. A radiation image of the object is thereby stored on the stimulable phosphor sheet. The stimulable phosphor sheet is then scanned two-dimensionally with stimulating rays, such as a laser beam, which cause it to emit light in proportion to the amount of energy stored thereon during its exposure to the radiation. The light emitted by the stimulable phosphor sheet, upon stimulation thereof, is photoelectrically detected by a photodetector and converted into an electric image signal.

In cases where a sheet of X-ray photographic film, a stimulable phosphor sheet, or the like, is exposed to radiation, which has passed through an object, a radiation image of the object being thereby recorded, or in cases where a radiation image of an object is formed and detected with an image intensifier, or the like, radiation which has been scattered by the object adversely affects the quality of the radiation image. Therefore, various attempts have heretofore been made to eliminate the scattered radiation during the operation for recording a radiation image.

For example, a slit exposure type of radiation image recording apparatus is disclosed in Japanese Unexamined Patent Publication No. 60(1985)-149043. With the disclosed radiation image recording apparatus, an object is scanned with linear radiation, which has passed through a slit. The linear radiation, which has passed through the object, is passed through a different slit and is then caused to impinge upon a radiation image storage means.

Also, multi-slit types of radiation image recording apparatuses are proposed in, for example, Japanese Unexamined Patent Publication No. 59(1984)-85650 and Med. Phy. 6(3), May/June 1979, pp. 197-204. With the proposed multi-slit types of radiation image recording apparatuses, a plurality of slits are utilized, and a radiation image is recorded with a plurality of streaks of linear radiation. Basically, the multi-slit type of radiation image recording apparatus comprises:

i) a radiation source for producing radiation, ii) a radiation image recording medium, which is located facing said radiation source, iii) a first slit plate composed of a radiation absorber and at least two slits, which are formed parallel to each other through said radiation absorber and through which said radiation passes, said first slit plate being located between said radiation source and an object, which object is placed between said radiation source and said radiation image recording medium, iv) a second slit plate composed of a radiation absorber and at least two slits, which are formed parallel to each other through said radiation absorber and through which said radiation passes, said second slit plate being located between said object and said radiation image recording medium such that at least two said slits of said second slit plate may be parallel to at least two said slits of said first slit plate, and v) a drive means for synchronously moving said first slit plate and said second slit plate in the direction, along which said slits stand side by side with each other, such that a plane, which passes through one of at least two said slits of said first slit plate and one of at least two said slits of said second slit plate, may pass through said radiation source.

However, with the radiation image recording apparatus disclosed in Japanese Unexamined Patent Publication No. 60(1985)-149043, the two slit plate located parallel to each other are linearly moved over the whole recording area of the radiation image recording medium. Therefore, the slits cannot be moved quickly. Accordingly, with this conventional radiation image recording apparatus, a long time is required for a single radiation image to be recorded, and the recording capacity cannot be kept high. Also, there is the risk that the object moves during the operation for recording a radiation image of the object and an artifact occurs easily. Additionally, the problem occurs in that the load of the radiation source cannot be kept low.

With the multi-slit type of radiation image recording apparatus, radiation images can be recorded quickly. However, if the distance, by which each slit moves within the time during which the radiation is irradiated, is not exactly equal to the intervals between the slits, some regions of the radiation image recording medium are scanned n times with the linear radiation, and the other regions of the radiation image recording medium are scanned n+1 times with the linear radiation. Therefore, the problem occurs in that artifacts occur at the boundaries between the regions scanned n times with the linear radiation and the regions scanned $n+1$ times with the linear radiation.

Also, for the radiation image recording apparatus wherein a plurality of slits are utilized, it is desired for a radiation image to be recorded quickly such that an artifact due to movement of an object during the operation for recording the radiation image of the object may be prevented from occurring. Additionally, the conventional radiation image recording apparatus, wherein a plurality of slits are utilized, has the drawbacks in that the apparatus cannot be kept small in size.

SUMMARY OF THE INVENTION

The primary object of the present invention is to provide a radiation image recording apparatus, in which adverse effects of scattered radiation are eliminated with a multi-slit exposure technique and with which a radiation image is recorded quickly such that no perceptible artifact may occur at boundaries between regions of a radiation image recording medium scanned at different times with linear radiation.

Another object of the present invention is to provide a radiation image recording apparatus, in which adverse effects of scattered radiation are eliminated with a slit exposure technique, with which a radiation image is recorded quickly, and which can be kept small in size.

The present invention provides a first radiation image recording apparatus which comprises:
i) a radiation source for producing radiation,
ii) a radiation image recording medium, which is located facing said radiation source,
iii) a first slit plate composed of a radiation absorber and at least two slits, which are formed parallel to each other and through which said radiation passes, said first slit plate being located between said radiation source and an object, which object is placed between said radiation source and said radiation image recording medium,
iv) a second slit plate composed of a radiation absorber and at least two slits, which are formed parallel to each other and through which said radiation passes, said second slit plate being located between said object and said radiation image recording medium such that at least two said slits of said second slit plate may be parallel to at least two said slits of said first slit plate, and
v) a drive means for synchronously moving said first slit plate and said second slit plate in the direction, along which said slits stand side by side with each other, such that a plane, which passes through one of at least two said slits of said first slit plate and one of at least two said slits of said second slit plate, may pass through said radiation source, wherein at least either one of said first slit plate and said second slit plate has a cross-sectional shape such that the thicknesses of walls, which extend on both sides of each said slit and define each said slit, may become progressively smaller towards each said slit.

With the first radiation image recording apparatus in accordance with the present invention, the first slit plate and the second slit plate ar moved synchronously in the direction, along which the slits stand side by side with each other, such that a plane, which passes through one of at least two slits of the first slit plate and one of at least two slits of the second slit plate, may pass through the radiation source. In this manner, the object is scanned with a plurality of streaks of linear radiation, which has passed through the slits of the first slit plate.

The linear radiation, which has passed through the object, passes through the slits of the second slit plate and then impinges upon the radiation image recording medium, such as a stimulable phosphor sheet or a sheet of X-ray photographic film. At this time, most of the radiation, which has been scattered by the object, is absorbed by the parts of the second slit plate other than its slits. Therefore, approximately only the primary radiation (i.e. the direct radiation), which has passed through the slits of the first slit plate and the slits of the second slit plate, impinges upon the radiation image recording medium. In this manner, a radiation image is recorded on the radiation image recording medium with the multi-slit exposure technique.

Also, with the first radiation image recording apparatus in accordance with the present invention, at least either one of the first slit plate and the second slit plate has the cross-sectional shape such that the thicknesses of walls, which extend on both sides of each slit and define the slit, may become progressively smaller towards the slit. Therefore, even if the distance, by which each slit plate moves within the time during which the radiation is irradiated, is different from the intervals between the slits, no perceptible artifact will occur at boundaries between regions of the radiation image recording medium scanned different times with the linear radiation. Specifically, as described above, depending on the distance by which each slit plate moves, some regions of the radiation image recording medium are scanned n times with the linear radiation, and the other regions of the radiation image recording medium are scanned $n+1$ times with the linear radiation. However, because the slit plate has the specific cross-sectional shape described above, the amount of the radiation, which impinged upon each of the ends of each region scanned $n+1$ times with the linear radiation (i.e. upon each part of each said region continuing to the adjacent region scanned n times with the linear radiation), becomes progressively smaller towards the adjacent region scanned n times with the linear radiation. Therefore, the amount of the radiation impinged changes comparatively gradually at the boundaries between the regions of the radiation image recording medium scanned n times with the linear radiation and the regions of the radiation image recording medium scanned $n+1$ times with the linear radiation. As a result, in the recorded radiation image, the image density changes comparatively gradually at the boundaries between the regions scanned different times with the linear radiation. Accordingly, no perceptible artifact occurs at the boundaries between the regions scanned different times with the linear radiation.

The present invention also provides a second radiation image recording apparatus which comprises:
i) a radiation source for producing radiation,
ii) a radiation image recording medium, which is located facing said radiation source,
iii) a first group of a plurality of cylindrical radiation absorbers, which are located between said radiation source and an object, which object is placed between said radiation source and said radiation image recording medium, such that the first group of the plurality of said cylindrical radiation absorbers may stand side by side with each other with small gaps intervening therebetween, each of the first group of the plurality of said cylindrical radiation absorbers being supported such that each said cylindrical radiation absorber can rotate around an eccentric shaft, which is shifted from a center axis of each said cylindrical radiation absorber, iv) a second group of a plurality of cylindrical radiation absorbers, which are located between said object and said radiation image recording medium such that the second group of the plurality of said cylindrical radiation absorbers may stand side by side with each other with small gaps intervening therebetween, each of the second group of the plurality of said cylindrical radiation absorbers being supported such that each said cylindrical radiation absorber can rotate around an eccentric shaft, which is shifted from a center axis of each said cylindrical radiation absorber, and v) a drive means for synchronously rotating the first group of the plurality of said cylindrical radiation absorbers and the second group of the plurality of said cylindrical radiation absorbers such that a plane, which passes through one of the small gaps intervening between the first group of the plurality of said cylindrical radiation absorbers and through one of the small gaps intervening between the second group of the plurality of said cylindrical radiation absorbers, may pass through said radiation source.

With the second radiation image recording apparatus in accordance with the present invention, the small gaps intervening between the first group of the plurality of the cylindrical radiation absorbers and the small gaps intervening between the second group of the plurality of the cylindrical radiation absorbers constitute slits. The first group of the plurality of the cylindrical radiation absorbers and the second group of the plurality of the cylindrical radiation absorbers are rotated synchronously such that a plane, which passes through one of the small gaps intervening between the first group of the plurality of the cylindrical radiation absorbers and through one of the small gaps intervening between the second group of the plurality of the cylindrical radiation absorbers, may pass through the radiation source. In this manner, the object is scanned with a plurality of streaks of linear radiation, which has passed through the small gaps intervening between the first group of the plurality of the cylindrical radiation absorbers. The linear radiation, which has passed through the object, passes through the small gaps intervening between the second group of the plurality of the cylindrical radiation absorbers and then impinges upon the radiation image recording medium, such as a stimulable phosphor sheet or a sheet of X-ray photographic film. At this time, most of the radiation, which has been scattered by the object, is absorbed by the second group of the plurality of the cylindrical radiation absorbers. Therefore, approximately only the primary radiation (i.e. the direct radiation), which has passed through the small gaps intervening between the first group of the plurality of the cylindrical radiation absorbers and through the small gaps intervening between the second group of the plurality of the cylindrical radiation absorbers, impinges upon the radiation image recording medium. In this manner, a radiation image is recorded o the radiation image recording medium with the slit exposure technique.

Also, with the second radiation image recording apparatus in accordance with the present invention, the first group of the plurality of the cylindrical radiation absorbers and the second group of the plurality of the cylindrical radiation absorbers can be rotated quickly. Therefore, the radiation image recording medium can be scanned quickly with the linear radiation. Accordingly, with the second radiation image recording apparatus in accordance with the present invention, the time required for a radiation image to be recorded can be kept shorter, the image recording capacity can be kept higher, and the load of the radiation source can be kept lower than in the conventional slit exposure type of radiation image recording apparatus, wherein a slit plate is moved linearly. Also, with the second radiation image recording apparatus in accordance with the present invention, little artifact is caused to occur by movement of the object during the slit exposure operation.

Additionally, with the second radiation image recording apparatus in accordance with the present invention, in cases where the first group of the plurality of the cylindrical radiation absorbers are composed of at least three cylindrical radiation absorbers and the second group of the plurality of the cylindrical radiation absorbers are composed of at least three cylindrical radiation absorbers, the slit exposure operation can be achieved simultaneously with at least two streaks of linear radiation. Therefore, the time required for a radiation image to be recorded can be reduced even further.

Moreover, the thickness of the structure of the plurality of the cylindrical radiation absorbers standing side by side with each other, which thickness is taken in the direction along which the radiation travels, can be kept substantially as small as the outer diameter of each radiation absorber. Therefore, the second radiation image recording apparatus in accordance with the present invention, wherein the slit exposure operation is carried out with such structures, can be kept small in size.

The present invention further provides a third radiation image recording apparatus which comprises:

i) a radiation source for producing radiation, ii) a radiation image recording medium, which is located facing said radiation source, iii) a first slit belt composed of a flexible, long strip-shaped, radiation-permeable substrate and a plurality of radiation absorbers, which are supported on said radiation-permeable substrate such that slit-like gaps may intervene between the plurality of said radiation absorbers, said first slit belt being located between said radiation source and an object, which object is placed between said radiation source and said radiation image recording medium, iv) a second slit belt composed of a flexible, long strip-shaped, radiation-permeable substrate and a plurality of radiation absorbers, which are supported on said radiation-permeable substrate such that slit-like gaps may intervene between the plurality of said radiation absorbers, said second slit belt being located between said object and said radiation image recording medium such that said slit-like gaps on said second slit belt may be parallel to said slit-like gaps on said first slit belt, v) a first belt moving means provided with rotatable members, which are engaged with said first slit belt and move said first slit belt in the direction, which is normal to the direction along which each said slit-like gap on said first slit belt extends, vi) a second belt moving means provided with rotatable members, which are engaged with said second slit belt and move said second slit belt in the direction, which is normal to the direction along which each said slit-like gap on said second slit belt extends, and vii) a control means for controlling said first belt moving means and said second belt moving means and synchronously moving said first slit belt and said second slit belt such that a plane, which passes through one of said slit-like gaps on said first slit belt and through one of said slit-like gaps on said second slit belt, may pass through said radiation source.

With the third radiation image recording apparatus in accordance with the present invention, the first slit belt and the second slit belt are moved synchronously such that a plane, which passes through one of the slit-like gaps on the first slit belt and through one of the slit-like gaps on the second slit belt, may pass through the radiation source. In this manner, the object is scanned with the linear radiation, which has passed through the slit-like gaps on the first slit belt. The linear radiation, which has passed through the object, passes through the slit-like gaps on the second slit belt and then impinges upon the radiation image recording medium, such as a stimulable phosphor sheet or a sheet of X-ray photographic film. At this time, most of the radiation, which has been scattered by the object, is absorbed by the radiation absorbers supported on the second slit belt. Therefore, approximately only the primary radiation (i.e. the direct radiation), which has passed through the slit-like gaps on the first slit belt and the slit-like gaps on the second slit belt, impinges upon the radiation image recording medium. In this manner, a radiation image is recorded on the radiation image recording medium with the slit exposure technique.

Also, with the third radiation image recording apparatus in accordance with the present invention, the rotatable members of the first belt moving means and the second belt moving means can be rotated quickly, and the first slit belt and the second slit belt can thereby be moved quickly. Therefore, the radiation image recording medium can be scanned quickly with the linear radiation. Accordingly, with the third radiation image recording apparatus in accordance with the present invention, the time required for a radiation image to be recorded can be kept shorter, and the image recording capacity can be kept higher than in the conventional slit exposure type of radiation image recording apparatus, wherein a slit plate is moved linearly. Also, with the third radiation image recording apparatus in accordance with the present invention, little artifact is caused to occur by movement of the object during the slit exposure operation.

Additionally, with the third radiation image recording apparatus in accordance with the present invention, in cases where the first slit belt and the second slit belt are moved a distance longer than the intervals between the slit-like gaps while the radiation is being produced by the radiation source, a single part of the radiation image recording medium is scanned several times with the linear radiation, and a radiation image is thereby recorded on the radiation image recording medium. Therefore, in the recorded radiation image, no perceptible artifact occurs at boundaries between regions scanned different times with the linear radiation.

DESCRIPTION OF THE PREFERRED EMBODIMENTS

The present invention will hereinbelow be described in further detail with reference to the accompanying drawings.

An embodiment of the first radiation image recording apparatus in accordance with the present invention will first be described hereinbelow with reference to FIG. 1A.

In this embodiment, a radiation image is recorded on a stimulable phosphor sheet 10. The stimulable phosphor sheet 10 is located at a predetermined position for exposure to radiation, and a radiation source 9, such as an X-ray tube, is located facing the stimulable phosphor sheet 10. When a radiation image of an object 8, such as a human body, is recorded, the object 8 is placed at a predetermined position between the radiation source 9 and the stimulable phosphor sheet 10.

Figure 1A:
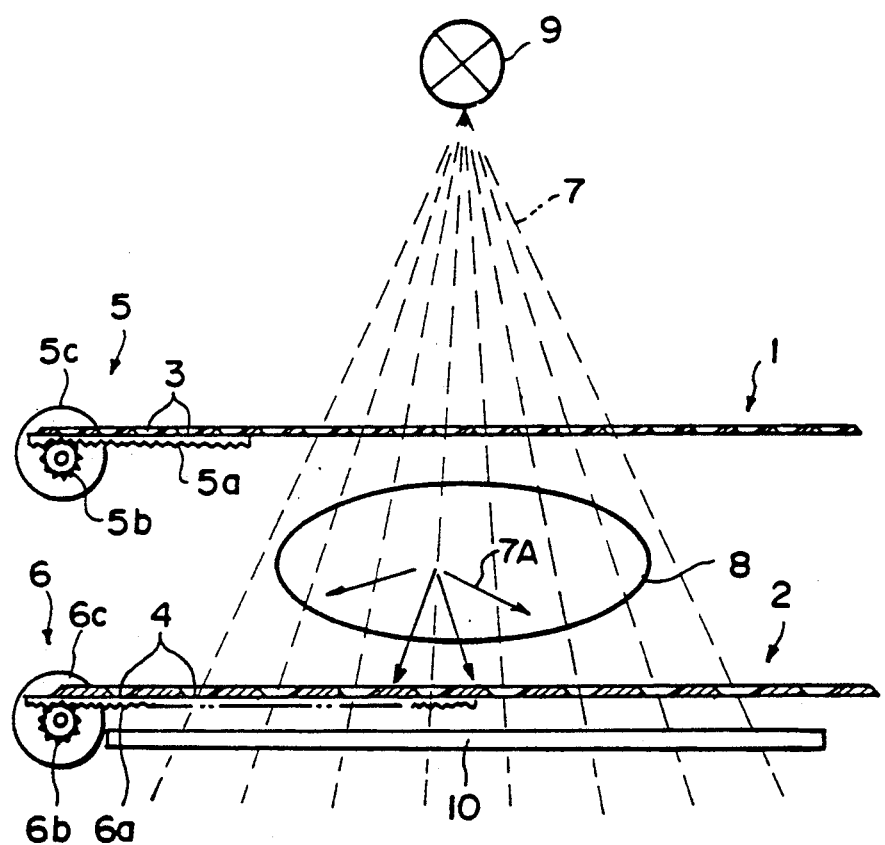
FIGS. 1A, 1B and 1C represent partially cutaway front views showing embodiments of the first radiation image recording apparatus including the slit configuration in the first and second slit plates in accordance with the present invention.
Figure 1B:
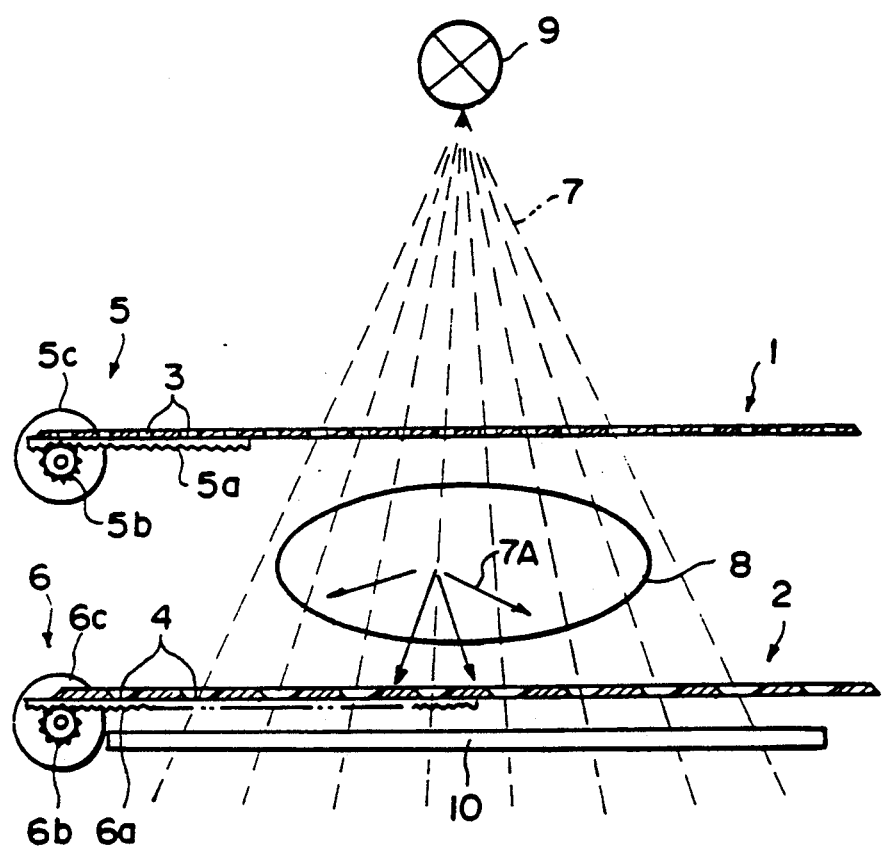

A first slit plate 1 is located such that it may intervene between the object 8 and the radiation source 9 when the object 8 is placed at the aforesaid position. The first slit plate 1 is constituted of a radiation absorber, such as a lead plate, and is provided with a plurality of slits 3, 3, . . . extending along a line normal to the plane of the sheet of FIG. 1. As shown in detail in FIG. 2, the first slit plate 1 has a cross-sectional shape such that the thicknesses of walls, which extend on both sides of each slit 3 and define the slit 3, may become progressively smaller towards the slit 3.

Also, a second slit plate 2 is located such that it may intervene between the object 8 and the stimulable phosphor sheet 10 when the object 8 is placed at the aforesaid position. As in the first slit plate 1, the second slit plate 2 is provided with a plurality of slits 4, 4, . . . Basically, the second slit plate 2 is constituted in the same manner as and has the same cross-sectional shape as the first slit plate 1, except that the widths of the slits 4, 4, ... and the intervals therebetween in the second slit plate 2 ar larger than the widths of the slits 3, 3, ... and the intervals therebetween in the first slit plate 1.

The first slit plate 1 and the second slit plate 2 are located such that the slits 3, 3, ... and the slits 4, 4, ... are parallel with each other. Also, the widths of the slits 3, 3, ... and the intervals therebetween in the first slit plate 1 and the widths of the slits 4, 4, ... and the intervals therebetween in the second slit plate 2 should preferably be set such that they may be proportional to the distances from the radiation source 9.

The first slit plate 1 is moved by a drive means 5 in the direction, along which the slits 3, 3, ... stand side by side with each other. The second slit plate 2 is moved by a drive means 6 in the direction, along which the slits 4, 4, ... stand side by side with each other. By way of example, the drive means 5 for moving the first slit plate 1 is constituted of a rack 5a, which is coupled with a side end of the first slit plate 1, a pinion 5b, which is engaged with the rack 5a, and a pulse motor 5c for rotating the pinion 5b. The pulse motor 5c rotates in forward and reverse directions in order to move the first slit plate 1 horizontally in FIG. 1. The drive means 6 for moving the second slit plate 2 is constituted of a rack 6a, which is coupled with a side end of the second slit plate 2, a pinion 6b, which is engaged with the rack 6a, and a pulse motor 6c for rotating the pinion 6b. The pulse motor 6c rotates in forward and reverse directions in order to move the second slit plate 2 horizontally in FIG. 1.

Figure 1C:
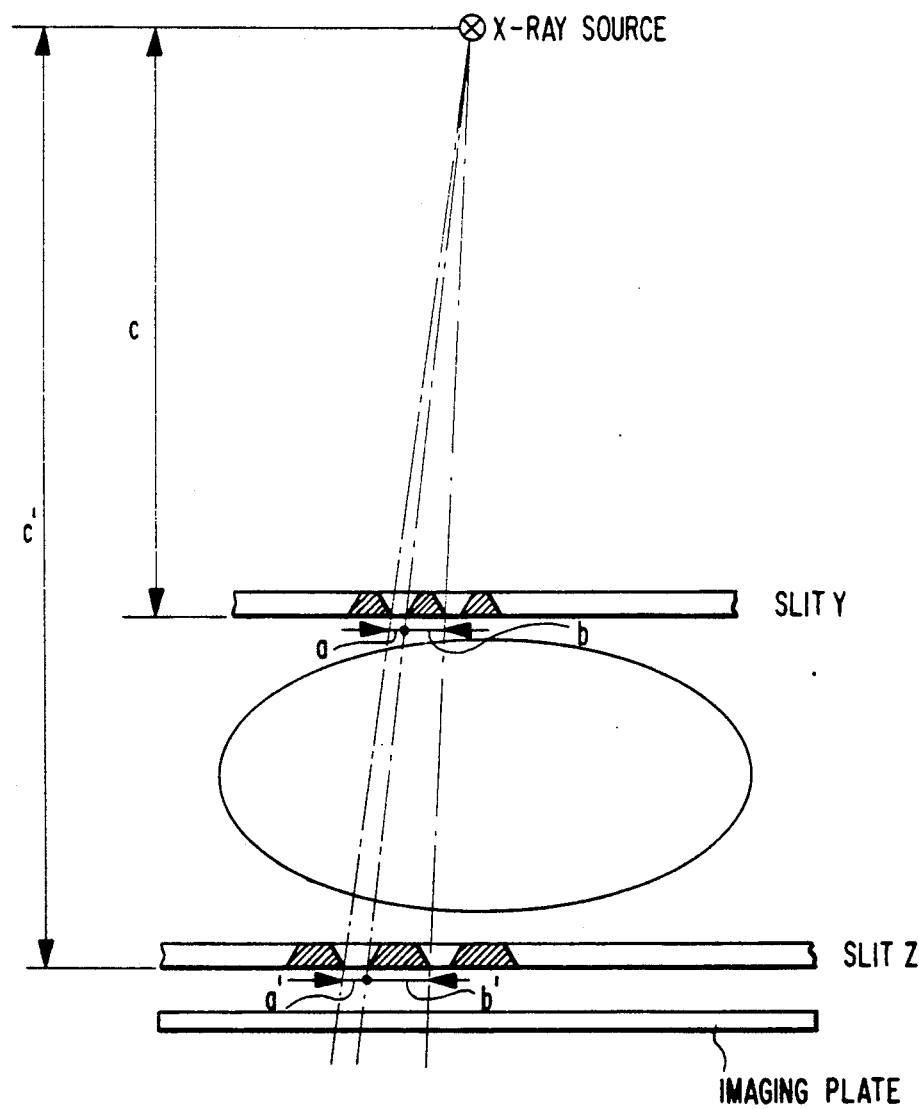
Figure 2:
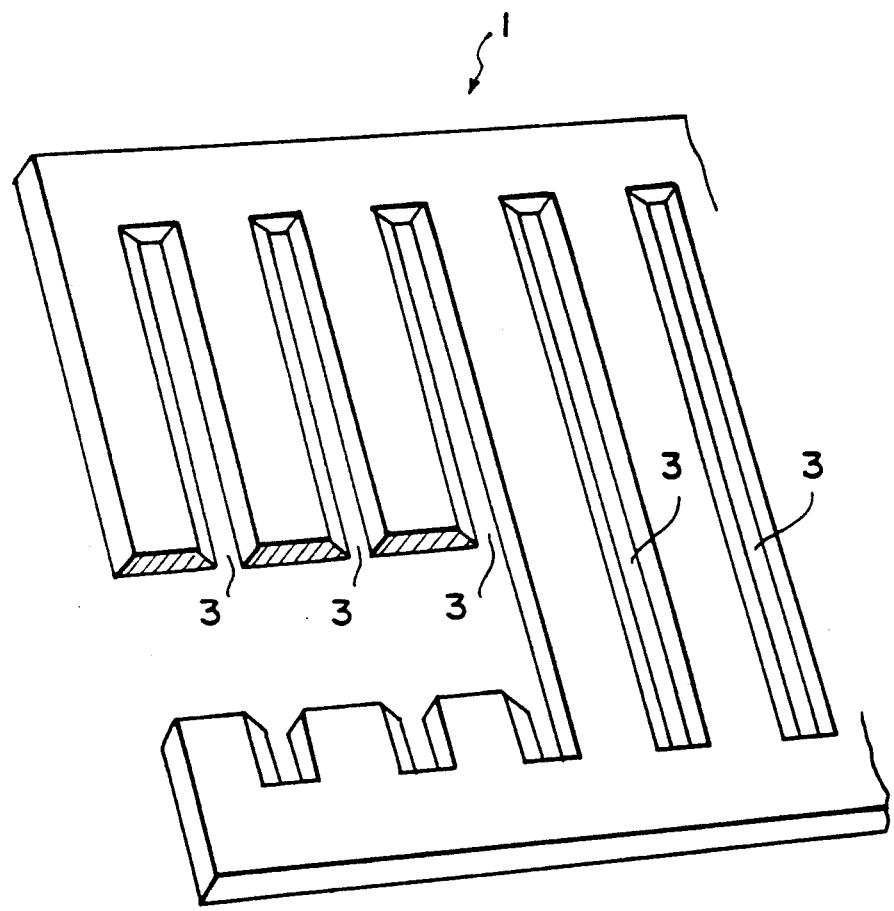
FIG. 2 is a partially cutaway perspective view showing the major part of the embodiment of FIG. 1A.

When a radiation image of the object 8 is recorded, the object 8 is placed at the position shown in FIG. 1, and the pulse motors 5c and 6c are then operated. In this manner, the first slit plate 1 and the second slit plate 2, which have been located at their right end positions in FIG. 1, are moved leftwardly. In this state, the radiation source 9 is activated to produce radiation 7 for a predetermined period of time, and the radiation 7 is irradiated to the object 8. The radiation 7 passes through the slits 3, 3, ... of the first slit plate 1. A plurality of streaks of the linear radiation 7, which has passed through the slits 3, 3, ..., pass through the object 8. At this time, as indicated by the arrows 7A, 7A, ..., part of the radiation 7 is scattered by the object 8. Most of the scattered radiation 7A is absorbed by the second slit plate 2. Therefore, approximately only the primary radiation (i.e. the direct radiation) impinges upon the stimulable phosphor sheet 10.

Also, at this time, a control circuit (not shown) controls the pulse motors 5c and 6c, and the first slit plate 1 and the second slit plate 2 are thereby moved synchronously such that a plane, which passes through one of the slits 3, 3, ... of the first slit plate 1 and through one of the slits 4, 4, ... of the second slit plate 2, may pass through the radiation source 9. When the first slit plate 1 and the second slit plate 2 are thus moved, the slits 3, 3, ... and the slits 4, 4, ... also move, and the object 8 is scanned with the linear radiation 7. In this manner, a radiation image of the object 8 is stored with the linear radiation 7 on the stimulable phosphor sheet 10.

As described above, most of the scattered radiation 7A is absorbed by the second slit plate 2. Therefore, the radiation image stored on the stimulable phosphor sheet 10 is not adversely affected by the scattered radiation 7A and has good image quality free of any noise.

When the operation for recording the radiation image is finished, the pulse motors 5c and 6c are rotated in reverse directions, and the first slit plate 1 and the second slit plate 2 are returned to their right end positions shown in FIG. 1A for the next operation for recording a radiation image.

Figure 3:
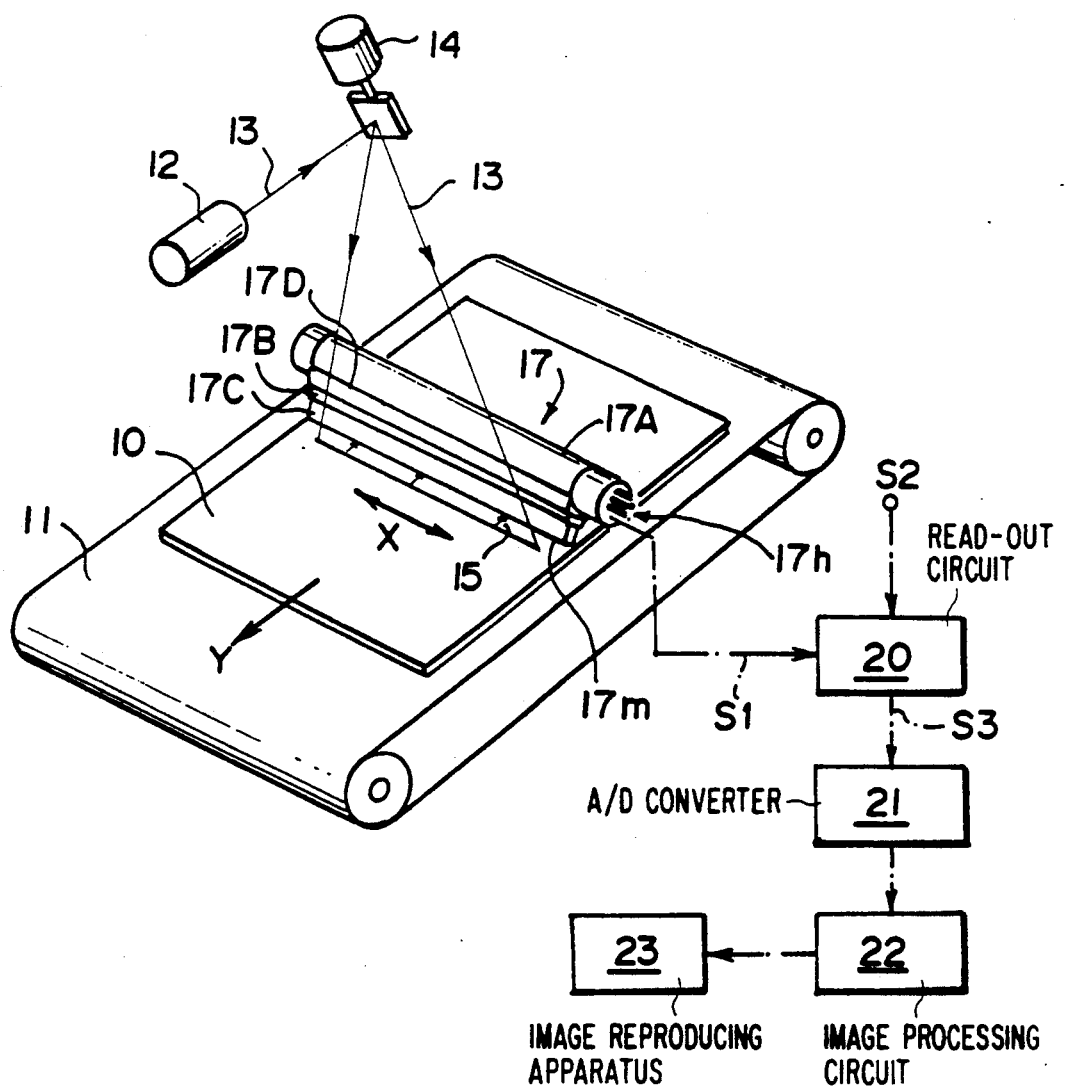
FIG. 3 is a schematic perspective view showing a radiation image read-out apparatus.

How the radiation image stored on the stimulable phosphor sheet 10 is read out and used in reproduction of a visible image will be described hereinbelow with reference to FIG. 3.

The stimulable phosphor sheet 10, on which the radiation image of the object 8 has been stored in the manner described above, is conveyed by a sheet conveyance means 11 in a sub-scanning direction indicated by the arrow Y. The sheet conveyance means 11 may be constituted of an endless belt, or the like. Also, a laser beam 13, which serves as stimulating rays, is produced by a laser beam source 12. The laser beam 13 is deflected by a light deflector 14 and is caused to scan the stimulable phosphor sheet 10 in main scanning directions indicated by the double headed arrow X, which directions are approximately normal to the sub-scanning direction indicated by the arrow Y. The light deflector 14 may be constituted of a galvanometer mirror, or the like. When the stimulable phosphor sheet 10 is thus exposed to the laser beam 13, the exposed portion of the stimulable phosphor sheet 10 emits light 15 in proportion to the amount of energy stored thereon during its exposure to the radiation.

The emitted light 15 is detected by a long photomultiplier 17. The long photomultiplier is disclosed in, for example, U.S. Pat. No. 4,864,134. An output S1 of the long photomultiplier 17, which output represents the amount of the emitted light 15, is fed into a read-out circuit 20, which carries out processing, such as amplification and logarithmic conversion, on the output S1. Also, the output S1 is integrated in units of a predetermined period in accordance with a synchronizing signal S2, which is synchronized to the scanning of the laser beam 13. In this manner, a serial analog read-out image signal S3, which has been divided into picture elements, is obtained from the read-out circuit 20. By way of example, the read-out image signal S3 is digitized by an A/D converter 21 and fed into an image processing circuit 22. The image processing circuit 22 carries out signal processing (image processing), such as gradation processing or frequency response processing, on the digital read-out image signal. The read-out image signal S3, which has been obtained from the signal processing, is fed into an image reproducing apparatus 23, which may be constituted of a CRT display device, a light beam scanning recording apparatus, or the like. The read-out image signal S3 is used in reproducing the radiation image, which was stored on the stimulable phosphor sheet 10, as a visible image.

Figure 4:
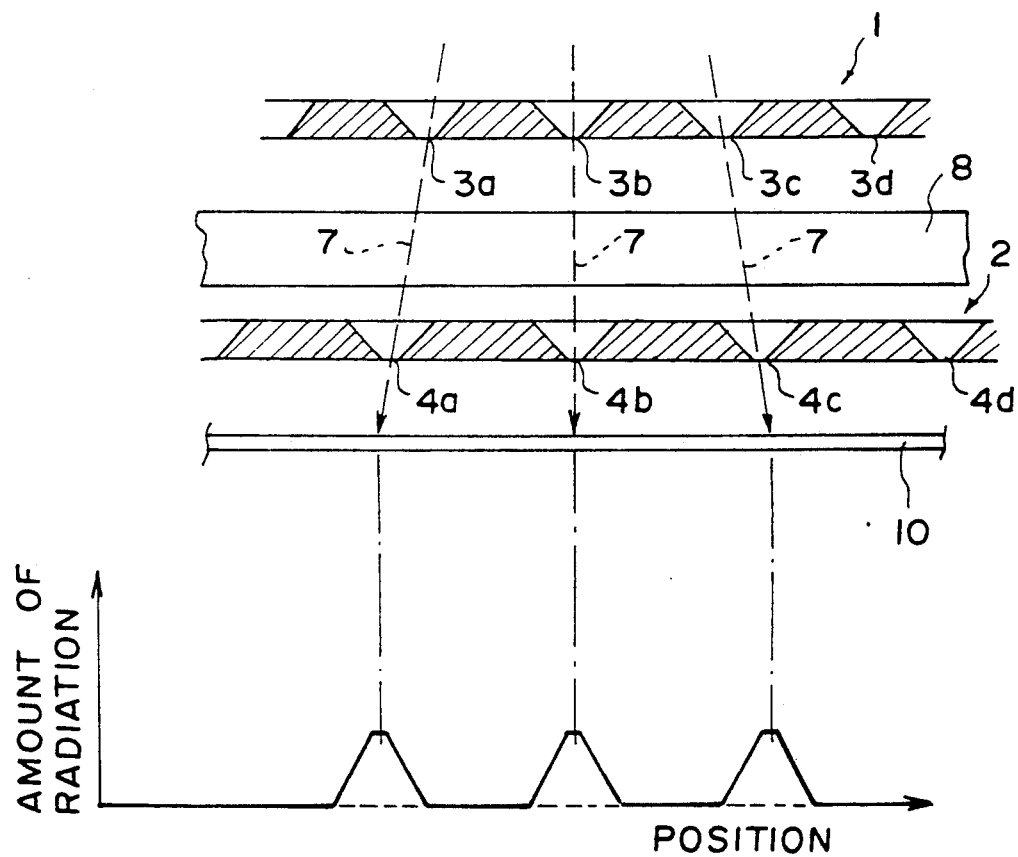
FIG. 4 is an explanatory view showing the effects of the first radiation image recording apparatus in accordance with the present invention.
Figure 5:
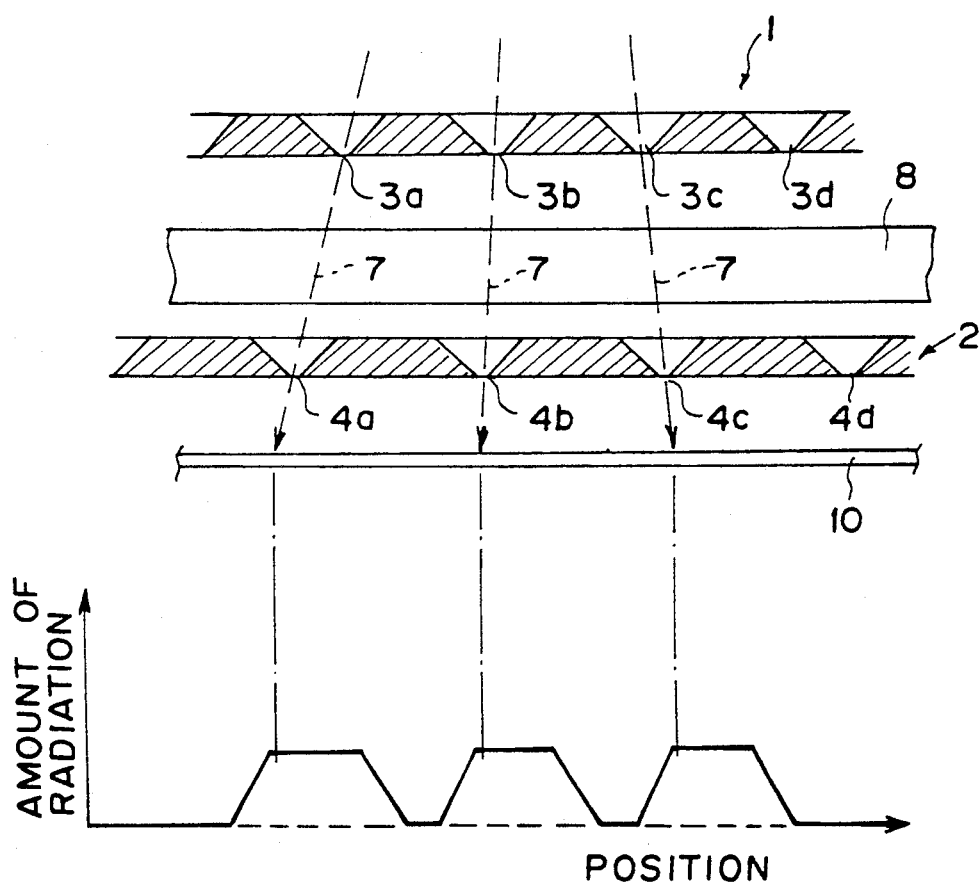
FIG. 5 is an explanatory view showing the effects of the first radiation image recording apparatus in accordance with the present invention.
Figure 6:
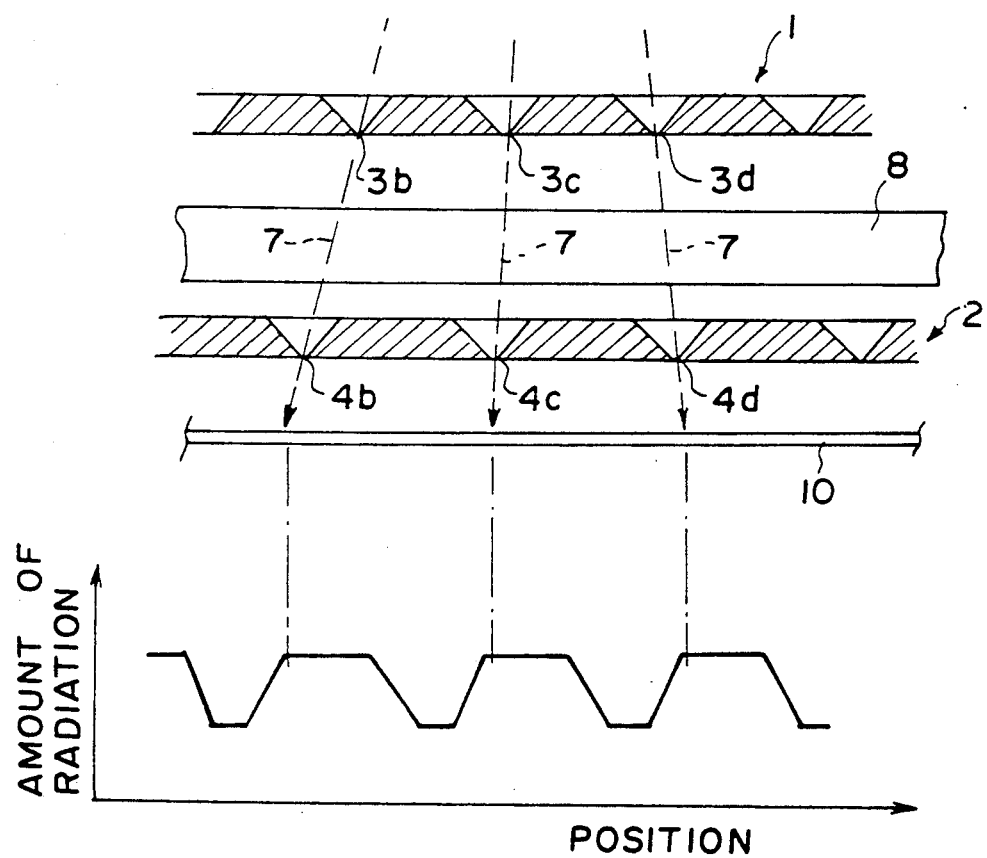
FIG. 6 is a explanatory view showing the effects of the first radiation image recording apparatus in accordance with the present invention.

In the radiation image, which has been recorded with the radiation image recording apparatus of FIG. 1A and reproduced in the manner described above, no perceptible artifact occurs at the boundaries between regions scanned at different times with the linear radiation 7. Such effects will be described hereinbelow with reference to FIGS. 4, 5, and 6. FIGS. 4, 5, and 6 schematically show the relationship between the positions of the slits 3, 3, ..., slits 4, 4, ... and the amount of the radiation 7 impinging upon the stimulable phosphor sheet 10. As an aid in facilitating the explanation, it is assumed that the amount of the primary radiation 7 impinging upon the slits 4, 4, ... of the second slit plate 2 is constant.

At the time at which the radiation source 9 begins to produce the radiation 7 while the first slit plate 1 and the second slit plate 2 are moving, the amount of the radiation 7 impinging upon the stimulable phosphor sheet 10 is distributed in the pattern shown in FIG. 4. As described above, the first slit plate 1 has a cross-sectional shape such that the thicknesses of walls, which extend on both sides of each slit 3 and define the slit 3, may become progressively smaller towards the slit 3. Also, the second slit plate 2 has a cross-sectional shape such that the thicknesses of walls, which extend on both sides of each slit 4 and define the slit 4, may become progressively smaller towards the slit 4. Therefore, as shown in FIG. 4, the distribution of the amount of the radiation 7 impinging upon the stimulable phosphor sheet 10 takes on the form of the pattern having mountain-like projecting parts.

At the time at which the first slit plate 1 has moved by a length shorter than the intervals between the slits 3, 3, . . . and the second slit plate 2 has moved by a length shorter than the intervals between the slits 4, 4, . . ., the amount of the radiation 7 impinging upon the stimulable phosphor sheet 10 is distributed in the pattern shown in FIG. 5. In FIGS. 4, 5, and 6, as an aid in explaining how long the slits 3, 3, . . . and the slits 4, 4, . . . have moved, characters a, b, c, . . . are attached to the reference numerals for these slits.

At the time at which the first slit plate 1 has moved by a length longer than the intervals between the slits 3, 3, . . . from the positions shown in FIG. 4 and the second slit plate 2 has moved by a length longer than the intervals between the slits 4, 4, . . . from the positions shown in FIG. 4, the amount of the radiation 7 impinging upon the stimulable phosphor sheet 10 is distributed in the pattern shown in FIG. 6. If the radiation source 9 is deactivated at this instant, regions, which have been scanned only once with the radiation 7, and regions, which have been scanned twice with the radiation 7, will occur alternately on the stimulable phosphor sheet 10 in the direction along which the slits 3, 3, . . . or the slits 4, 4, . . . stand side by side with each other. The amount of the radiation 7 having impinged upon the regions, which have been scanned twice with the radiation 7, is larger than the amount of the radiation 7 having impinged upon the regions, which have been scanned only once with the radiation 7. However, as described above, the distribution of the amount of the radiation 7 impinging upon the stimulable phosphor sheet 10 takes on the form of the pattern having mountain-like projecting parts. Therefore, the amount of the radiation 7 having impinged upon the stimulable phosphor sheet 10 becomes gradually smaller from the regions which have been scanned twice with the radiation 7, towards the regions, which have been scanned only once with the radiation 7. Accordingly, no perceptible artifact is caused to occur by the difference in the amount of the radiation 7, which has impinged upon the stimulable phosphor sheet 10, at the boundaries between the regions, which have been scanned only once with the radiation 7, and the regions, which have been scanned twice with the radiation 7.

In cases where the regions, which have been scanned only once with the radiation 7, and the regions, which have been scanned twice with the radiation 7, occur alternately on the stimulable phosphor sheet 10, the embodiment of FIG. 1 has the effects described above. Also, in the same manner as that described above, when the radiation 7 is irradiated for a longer time onto the stimulable phosphor sheet 10, and regions, which have been scanned n times (wherein $2 \leq n$) with the radiation 7, and regions, which have been scanned $n+1$ times with the radiation 7, occur on the stimulable phosphor sheet 10, no perceptible artifact occurs in the recorded radiation image between the regions scanned different times with the radiation.

In the embodiment of FIG. 1A the first slit plate 1 has the cross-sectional shape such that the thicknesses of walls, which extend on both sides of each slit 3 and define the slit 3, may become progressively smaller towards the slit 3. Also, the second slit plate 2 has the cross-sectional shape such that the thicknesses of walls, which extend on both sides of each slit 4 and define the slit 4, may become progressively smaller towards the slit 4. Alternatively, only either one of the first slit plate 1 and the second slit plate 2 may have such a specific cross-sectional shape, as illustrated in FIG. 1B. In such cases, the same effects as the embodiment of FIG. 1 can be obtained.

Also, in the embodiment of FIG. 1A, the first slit plate 1 and the second slit plate 2 constituted in the manner described above are employed. Alternatively, each of the slit plates may be constituted of a radiation-permeable plate-like member or a flexible, long strip-shaped member, and a plurality of radiation absorbers, which are located on the radiation-permeable plate-like member or a flexible, long strip-shaped member such that slit-like gaps intervene between the radiation absorbers.

An embodiment of the second radiation image recording apparatus in accordance with the present invention will be described hereinbelow with reference to FIG. 7.

In this embodiment, a radiation image is recorded on a stimulable phosphor sheet 10. The stimulable phosphor sheet 10 is located at a predetermined position for exposure to radiation, and a radiation source 9, such as an X-ray tube, is located facing the stimulable phosphor sheet 10. When a radiation image of an object 8, such as a human body, is recorded, the object 8 is placed at a predetermined position between the radiation source 9 and the stimulable phosphor sheet 10.

A first group of a plurality of (by way of example, eight) cylindrical radiation absorbers 101, 101, . . . are located between the radiation source 9 and the stimulable phosphor sheet 10. The first group of the cylindrical radiation absorbers 101, 101, . . . stand side by side with small gaps intervening therebetween. By way of example, the first group of the cylindrical radiation absorbers 101, 101, . . . are constituted of lead. The first group of the cylindrical radiation absorbers 101, 101, . . . are provided such that, when the object 8 is placed at the predetermined position for exposure to the radiation 7, the first group of the cylindrical radiation absorbers 101, 101, . . . may be positioned between the radiation source 9 and the object 8.

Also, a second group of a plurality of (by way of example, eight) cylindrical radiation absorbers 102, 102, . . . are located side by side with small gaps intervening therebetween. By way of example, the second group of the cylindrical radiation absorbers 102, 102, . . . are constituted of lead. The second group of the cylindrical radiation absorbers 102, 102, . . . are provided such that, when the object 8 is placed at the predetermined position for exposure to the radiation 7, the second group of the cylindrical radiation absorbers 102, 102, . . . may be positioned between the object 8 and the stimulable phosphor sheet 10.

Figure 9:
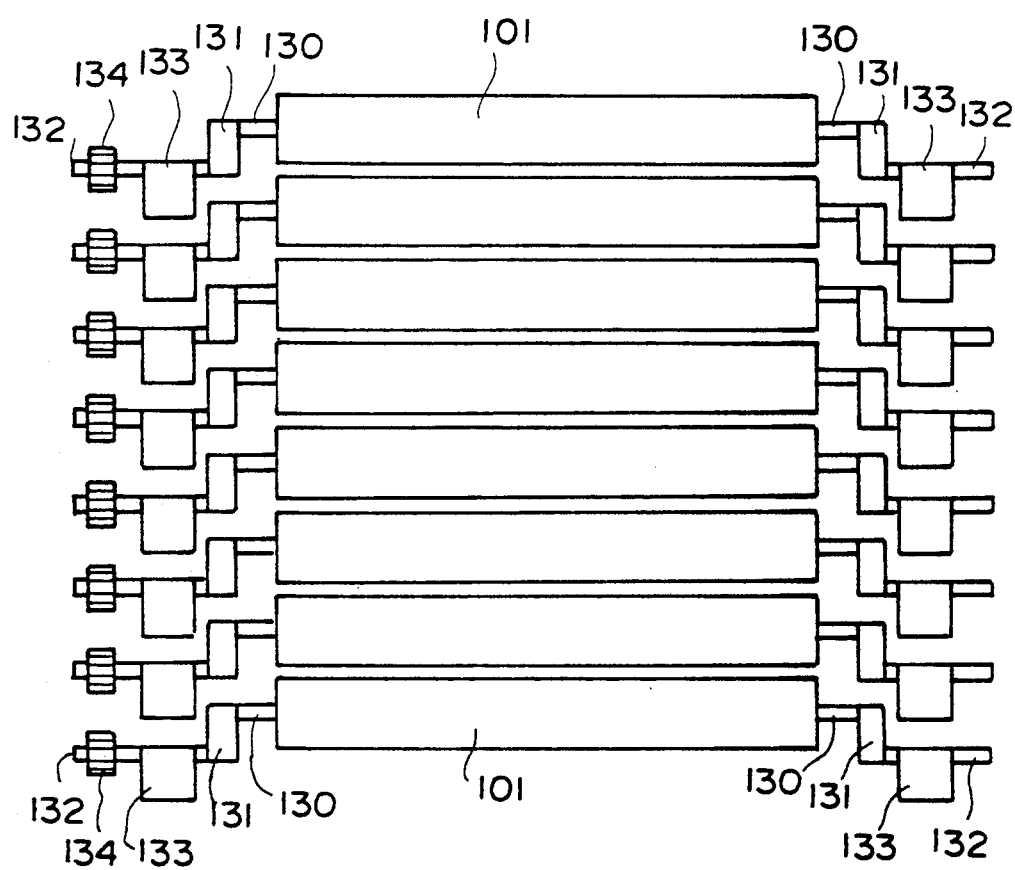
FIG. 9 is a plan view showing the major part of the embodiment of FIG. 7.

FIG. 9 shows the first group of the cylindrical radiation absorbers 101, 101, . . . and the surrounding parts. As shown in FIG. 9, shafts 130, 130, which are coaxial with the center of each cylindrical radiation absorber 101, are secured to both ends of each cylindrical radiation absorber 101. Each of the shafts 130, 130 is connected to an eccentric shaft 132 via a coupling member 131, which extends in the radial direction of the cylindrical radiation absorber 101. The two eccentric shafts 132, 132 on both sides of the cylindrical radiation absorber 101 are supported on bearing devices (not shown). The cylindrical radiation absorber 101 can rotate around the eccentric shafts 132, 132. A counter weight 133 is secured to each eccentric shaft 132 such that the cylindrical radiation absorber 101, which is comparatively heavy, can rotate easily. Also, a gear 134 is secured to one of the two eccentric shafts 132, 132, which are connected to each cylindrical radiation absorber 101.

Figure 7:
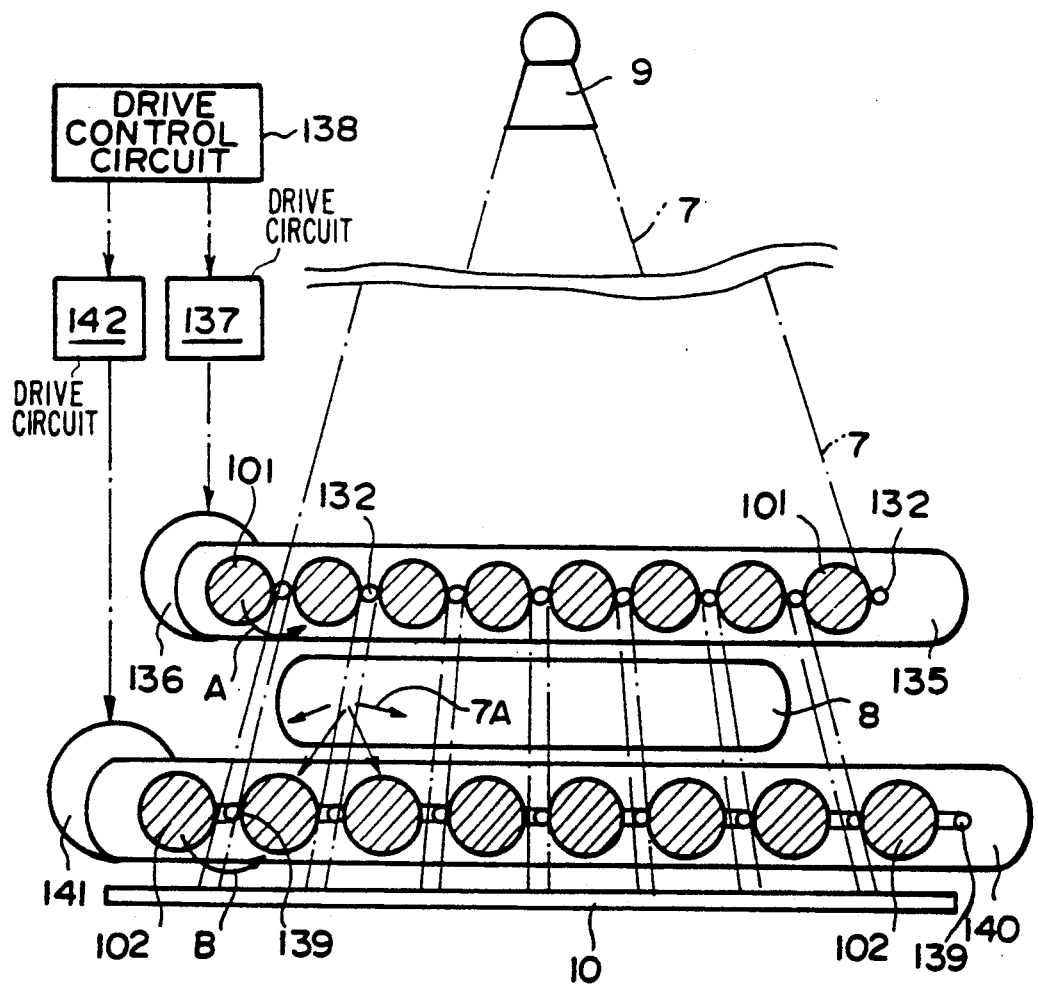
FIG. 7 is a partially cutaway front view showing an embodiment of the second radiation image recording apparatus in accordance with the present invention.

The gears 134, 134, . . . which are secured to the eccentric shafts 132, 132, . . . connected to the first group of the cylindrical radiation absorbers 101, 101, . . . are engaged with gears of a driving force transmitting mechanism 135, which is shown in FIG. 7. The driving force transmitting mechanism 135 transmits the rotating force of a motor 136, which may be constituted of a servo motor, or the like, to each eccentric shaft 132 via each gear 134. Therefore, when the motor 136 operates, the first group of the cylindrical radiation absorbers 101, 101, . . . are rotated around the corresponding eccentric shafts 132, 132, . . . In FIG. 7, the direction of rotation of the cylindrical radiation absorber 101, which is located on the extreme left side, is indicated by the arrow A. The motor 136 receives a driving current from a drive circuit 137 and is thereby operated. The motor 136 is controlled by a drive control circuit 138.

Basically, the second group of the cylindrical radiation absorbers 102, 102, . . . are constituted in the same manner as that in the first group of the cylindrical radiation absorbers 101, 101, . . . except that the outer diameter of and the intervals between the second group of the cylindrical radiation absorbers 102, 102, . . . are larger than those of the first group of the cylindrical radiation absorbers 101, 101, . . . The second group of the cylindrical radiation absorbers 102, 102, . . . can rotate around eccentric shafts 139, 139, . . . which are of the same type as the eccentric shafts 132, 132, . . . connected to the first group of the cylindrical radiation absorbers 101, 101, . . . The driving force of a motor 141 is transmitted to the second group of the cylindrical radiation absorbers 102, 102, . . . via a driving force transmitting mechanism 140. Specifically, when the motor 141 operates, the second group of the cylindrical radiation absorbers 102, 102, . . . are rotated around the corresponding eccentric shafts 139, 139, . . . In FIG. 7, the direction of rotation of the cylindrical radiation absorber 102, which is located on the extreme left side, is indicated by the arrow B. The motor 141 receives a driving current from a drive circuit 142 and is thereby operated. The motor 141 is controlled by the drive control circuit 138.

Figure 8:
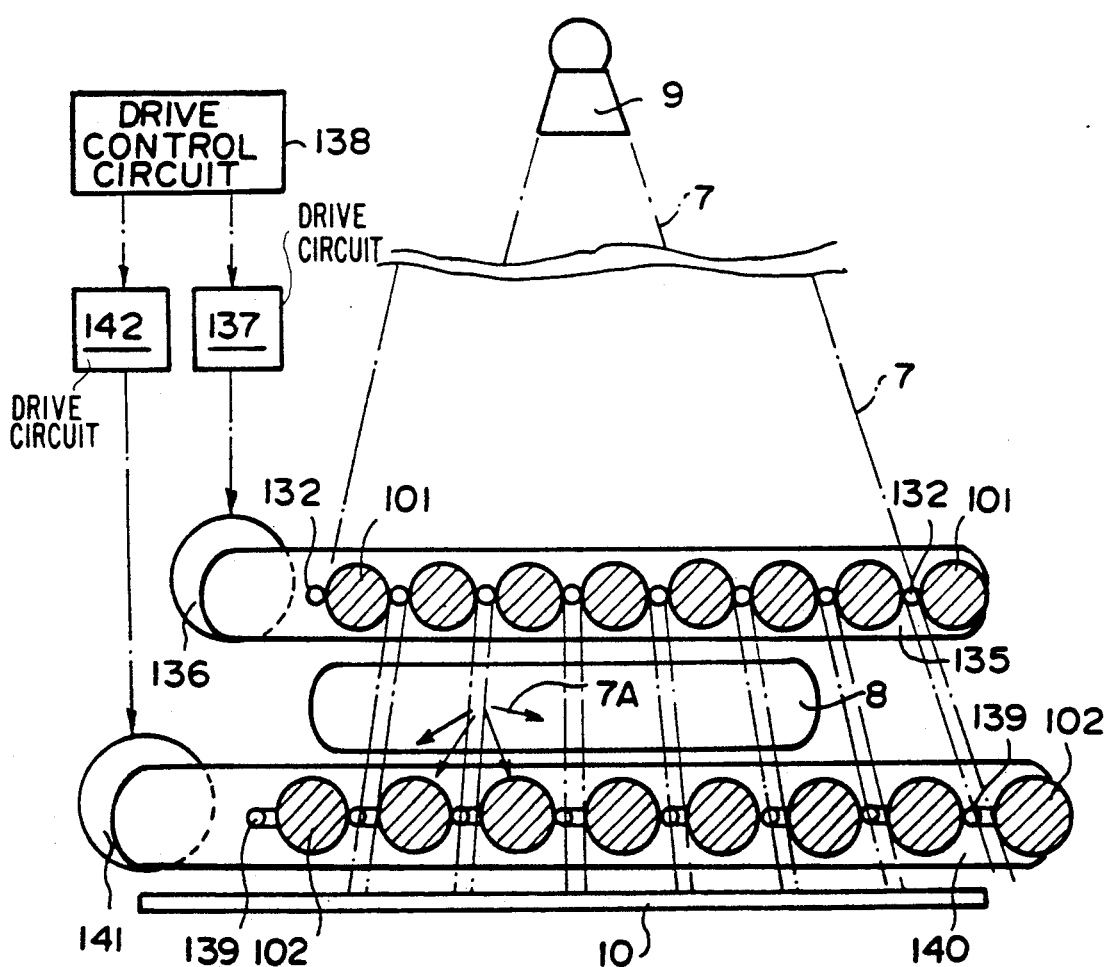
FIG. 8 is a partially cutaway front view showing the embodiment of FIG. 7, which is in a different state.

When a radiation image of the object 8 is recorded, the object 8 is placed at the position shown in FIGS. 7 and 8, and the motors 136 and 141 are then operated. In this manner, the first group of the cylindrical radiation absorbers 101, 101, . . . are rotated around the eccentric shafts 132, 132, . . . Also, the second group of the cylindrical radiation absorbers 102, 102, . . . are rotated around the eccentric shafts 139, 139, . . . In this state, the radiation source 9 is activated to produce the radiation 7 for a predetermined period of time, and the radiation 7 is irradiated to the object 8. The radiation 7 passes through the slit-like gaps between the first group of the (eight) cylindrical radiation absorbers 101, 101, . . . A plurality of (in this case, seven) streaks of the linear radiation 7, which has passed through the slit-like gaps, pass through the object 8. At this time, as indicated by the arrows 7A, 7A, . . . part of the radiation 7 is scattered by the object 8. Most of the scattered radiation 7A is absorbed by the second group of the cylindrical radiation absorbers 102, 102, . . . Therefore, approximately only the primary radiation (i.e. the direct radiation) impinges upon the stimulable phosphor sheet 10.

Also, at this time, the drive control circuit 138 controls the motors 136 and 141. In this manner, the first group of the cylindrical radiation absorbers 101, 101, . . . and the second group of the cylindrical radiation absorbers 102, 102, . . . are rotated synchronously such that a plane, which passes through one of the slit-like gaps between the first group of the cylindrical radiation absorbers 101, 101, . . . and through one of the slit-like gaps between the second group of the cylindrical radiation absorbers 102, 102, . . . may pass through the radiation source 9. FIG. 8 shows the first group of the cylindrical radiation absorbers 101, 101, . . . and the second group of the cylindrical radiation absorbers 102, 102, . . . which have rotated 180° from the positions shown in FIG. 7. When the first group of the cylindrical radiation absorbers 101, 101, . . . and the second group of the cylindrical radiation absorbers 102, 102, . . . are thus rotated, the slit-like gaps between the first group of the cylindrical radiation absorbers 101, 101, . . . and the slit-like gaps between the second group of the cylindrical radiation absorbers 102, 102, . . . move. The object 8 is thus scanned with the linear radiation 7. In this manner, a radiation image of the object 8 is stored with the linear radiation 7 on the stimulable phosphor sheet 10.

As described above, most of the scattered radiation 7A is absorbed by the second group of the cylindrical radiation absorbers 102, 102, . . . Therefore, the radiation image stored on the stimulable phosphor sheet 10 is not adversely affected by the scattered radiation 7A and has good image quality free of any noise.

Also, the first group of the cylindrical radiation absorbers 101, 101, . . . and the second group of the cylindrical radiation absorbers 102, 102, . . . can be rotated quickly. Therefore, the stimulable phosphor sheet 10 can be scanned quickly with the linear radiation 7. Accordingly, with this embodiment of the second radiation image recording apparatus in accordance with the present invention, the time required for a radiation image to be recorded can be kept short, the image recording capacity can be kept high, and the load of the radiation source 9 can be kept low. Also, with this embodiment, little artifact is caused to occur by movement of the object 8 during the slit exposure operation. Additionally, with this embodiment, the slit exposure operation can be achieved simultaneously with the seven streaks of the linear radiation 7. Therefore, the time required for a radiation image to be recorded can be reduced even further.

Moreover, the thickness of the structures of the first group of the cylindrical radiation absorbers 101, 101, . . . standing side by side with each other and the second group of the cylindrical radiation absorbers 102, 102, . .

standing side by side with each other, which thickness is taken in the direction along which the radiation 7 travels, can be kept substantially as small as the sum of the outer diameters of each radiation absorber 101 and each radiation absorber 102. Therefore, this embodiment of the second radiation image recording apparatus in accordance with the present invention, wherein the slit exposure operation is carried out with such structures, can be kept small in size.

The radiation image, which has been stored on the stimulable phosphor sheet 10, is read out in the same manner as that described above with reference to FIG. 3, and the read-out image signal thus obtained is used in reproducing a visible image.

The embodiment of FIG. 7 is provided with the first group of the cylindrical radiation absorbers 101, 101, . . . and the second group of the cylindrical radiation absorbers 102, 102, . . . which have a true circular cross-sectional shape. Alternatively, cylindrical radiation absorbers having an elliptic cross-sectional shape may be employed such that the speed, with which each slit-like gap moves, may not change depending on the position, to which each radiation absorber rotates. In cases where the speed, with which each slit-like gap moves, is thus made uniform, the problem can be prevented from occurring in that the amount of the radiation impinging upon the radiation image recording medium is caused to vary by fluctuations in the speed, with which each slit-like gap moves.

The first group of the cylindrical radiation absorbers 101, 101, . . . should preferably be located such that the widths of the slit-like gaps formed between the radiation absorbers, which are located at the ends of the array of the cylindrical radiation absorbers, may be comparatively large, and the widths of the slit-like gaps formed between the cylindrical radiation absorbers, which are located at the middle of the array of the cylindrical radiation absorbers, may be comparatively small. Also, the second group of the cylindrical radiation absorbers 102, 102, . . . should preferably be located such that the widths of the slit-like gaps formed between the radiation absorbers, which are located at the ends of the array of the cylindrical radiation absorbers, may be comparatively large, and the widths of the slit-like gaps formed between the cylindrical radiation absorbers, which are located at the middle of the array of the cylindrical radiation absorbers, may be comparatively small. In such cases, the solid angles of the plurality of the streaks of the linear radiation can be made equal to each other.

Additionally, in the embodiment of FIG. 7, the first group of the cylindrical radiation absorbers 101, 101, . . . are arrayed along a straight line. Also, the second group of the cylindrical radiation absorbers 102, 102, . . . are arrayed along a straight line. Alternatively, the first group of a plurality of cylindrical radiation absorbers, the second group of a plurality of cylindrical radiation absorbers, and the radiation image recording medium may be located along arcs of three concentric circles having their centers at the focal point of the radiation source 9. In such cases, the widths of the plurality of the streaks of the linear radiation can be made equal to each other.

An embodiment of the third radiation image recording apparatus in accordance with the present invention will be described hereinbelow with reference to FIG. 10.

In this embodiment, a radiation image is recorded on a stimulable phosphor sheet 10. The stimulable phosphor sheet 10 is located at a predetermined position for exposure to radiation, and a radiation source 9, such as an X-ray tube, is located facing the stimulable phosphor sheet 10. When a radiation image of an object 8, such as a human body, is recorded, the object 8 is placed at a predetermined position between the radiation source 9 and the stimulable phosphor sheet 10.

Figure 11:
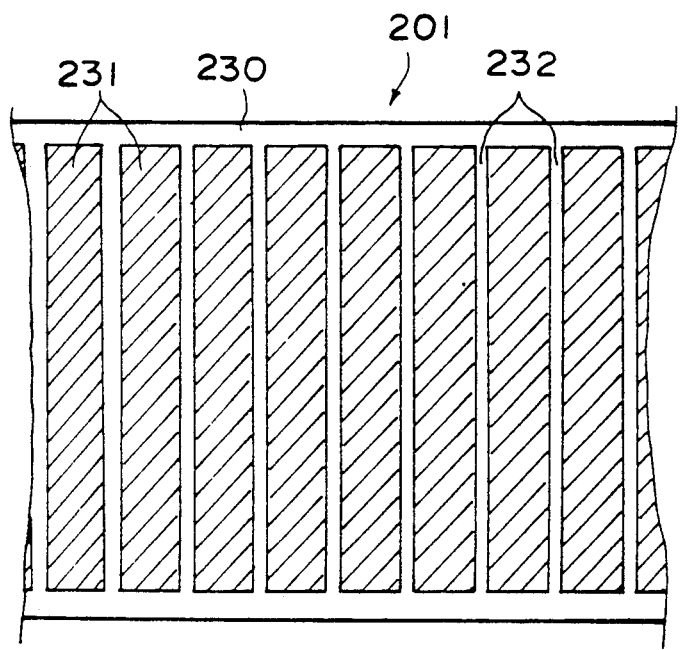
FIG. 11 is a plan view showing the major part of the embodiment of FIG. 10.

A first slit belt 201 is positioned between the radiation source 9 and the stimulable phosphor sheet 10. As illustrated in FIG. 11, the first slit belt 201 is composed of a flexible, long strip-shaped, radiation-permeable substrate 230 and a plurality of radiation absorbers 231, 231, . . . which are supported on the radiation-permeable substrate 230 such that slit-like gaps 232, 232, . . . may intervene between the plurality of radiation absorbers 231, 231, . . . The radiation absorbers 231, 231, . . . stand side by side along the longitudinal direction of the radiation-permeable substrate 230. By way of example, the radiation-permeable substrate 230 may be constituted of polyethylene terephthalate, or the like. The radiation absorbers 231, 231, . . . may be constituted of a heavy metal, such as tantalum, tungsten, lead, bismuth, gold, or platinum, or a heavy element compound, such as tungstate, basic lead carbonate, or a rare earth metal oxide. In such cases, the heavy metal or the heavy element compound is dispersed in a polymer, and the resulting dispersion is applied onto the radiation-permeable substrate 230 with a screen printing process, or the like.

Both ends of the first slit belt 201 are supported by a wind-up shaft 233 and a wind-up shaft 234, respectively, and the first slit belt 201 is thereby positioned between the wind-up shaft 233 and the wind-up shaft 234. The first slit belt 201 is provided such that, when the object 8 is placed at the predetermined position for exposure to the radiation 7, the first slit belt 201 may be positioned between the radiation source 9 and the object 8. The wind-up shaft 233 is rotated counter-clockwise in FIG. 10 by a motor 235, which may be constituted of a servo motor, or the like. The motor 235 receives a driving current from a drive circuit 236 and is thereby operated. The motor 235 is controlled by a drive control circuit 250. The wind-up shaft 234 is rotated clockwise in FIG. 10 by a motor 238.

Figure 10:
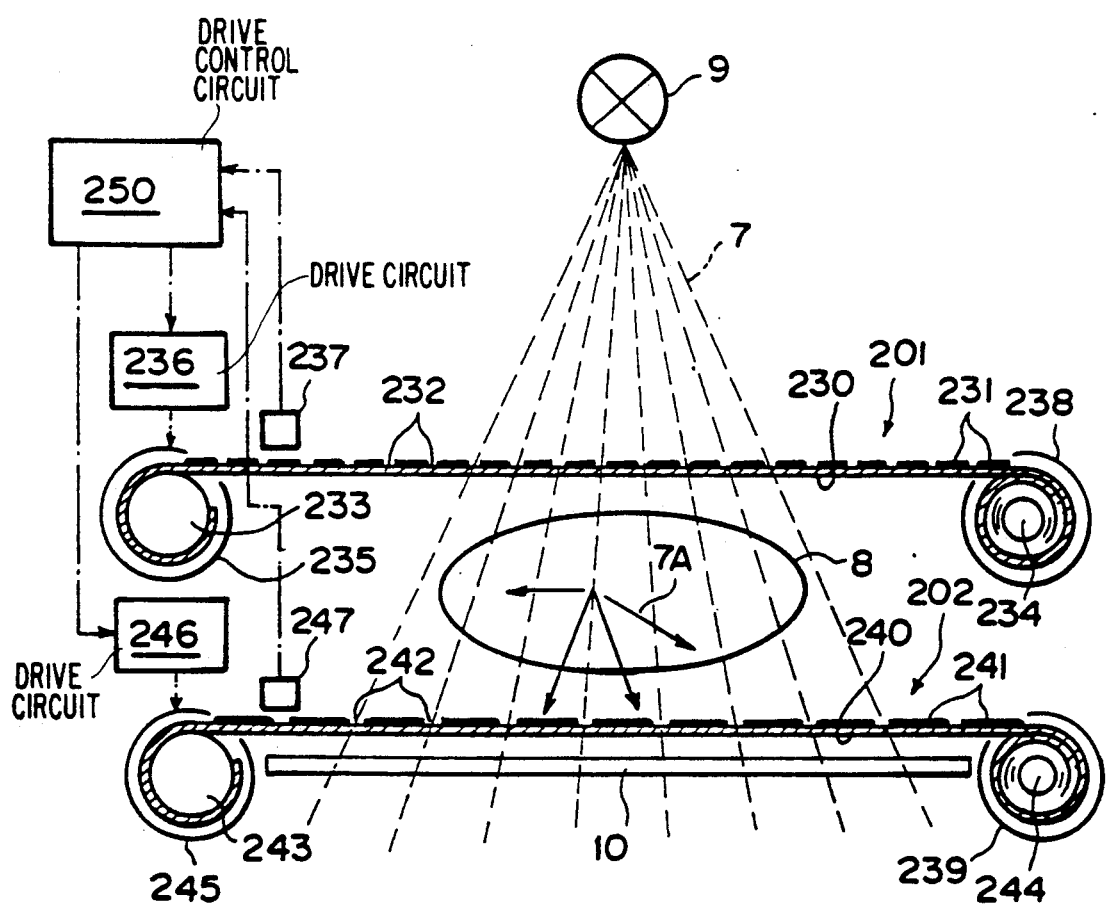
FIG. 10 is a partially cutaway front view showing an embodiment of the third radiation image recording apparatus in accordance with the present invention.

When the motor 235 operates, the first slit belt 201 is wound up around the wind-up shaft 233 and moved leftwardly in FIG. 10. At this time, the speed, with which the first slit belt 201 moves, is detected by an encoder 237. Specifically, the radiation-permeable substrate 230 and the radiation absorbers 231, 231, . . . have different light reflectivities. The encoder 237 irradiates light onto the first slit belt 201 and receives the light reflected from the first slit belt 201. The encoder 237 detects the speed, with which the first slit belt 201 moves, from a periodic change in the amount of reflected light due to the difference in the light reflectivity between the radiation-permeable substrate 230 and the radiation absorbers 231, 231, . . . The output of the encoder 237 is fed into the drive control circuit 250.

A second slit belt 202 is located such that, when the object 8 is placed at the predetermined position for exposure to the radiation 7, the second slit belt 202 intervenes between the object 8 and the stimulable phosphor sheet 10. As in the first slit belt 201, the second slit belt 202 is composed of a flexible, long strip-shaped, radiation-permeable substrate 240 and a plurality of radiation absorbers 241, 241, . . . which are supported on the radiation-permeable substrate 240 such that slit-like gaps 242, 242, . . . may intervene between the plurality of radiation absorbers 241, 241, . . . The radiation absorbers 241, 241, . . . stand side by side along the longitudinal direction of the radiation-permeable substrate 240. The radiation-permeable substrate 240 of the second slit belt 202 is constituted in the same manner as that of the radiation-permeable substrate 230 of the first slit belt 201. Also, basically, the radiation absorbers 241, 241, . . . on the second slit belt 202 are constituted in the same manner as that of the radiation absorbers 231, 231, . . . on the first slit belt 201, except that the widths of the radiation absorbers 241, 241, . . . and the slit-like gaps 242, 242, . . . therebetween on the second slit belt 202 are larger than the widths of the radiation absorbers 231, 231, . . . and the slit-like gaps 232, 232, . . . therebetween on the first slit belt 201.

The widths of the slit-like gaps 232, 232, . . . and the intervals therebetween on the first slit belt 201 and the widths of the slit-like gaps 242, 242, . . . and the intervals therebetween on the second slit belt 202 should preferably be set such that they may be proportional to the distances from the radiation source 9. Also, the thicknesses of the radiation absorbers 231, 231, . . . and the radiation absorbers 241, 241, . . . should preferably be approximately 500 $\mu$m.

Both ends of the second slit belt 202 are supported by a wind-up shaft 243 and a wind-up shaft 244, respectively, and the second slit belt 202 is thereby positioned between the wind-up shaft 243 and the wind-up shaft 244. The wind-up shaft 243 is rotated counterclockwise in FIG. 10 by a motor 245, which may be constituted of a servo motor, or the like. The motor 245 receives a driving current from a drive circuit 246 and is thereby operated. The motor 245 is controlled by the drive control circuit 250. The wind-up shaft 244 is rotated clockwise in FIG. 10 by a motor 239.

When the motor 245 operates, the second slit belt 202 is wound up around the wind-up shaft 243 and moved leftwardly in FIG. 10. At this time, the speed, with which the second slit belt 202 moves, is detected by an encoder 247. The encoder 247 is of the same type as the encoder 237. The output of the encoder 247 is fed into the drive control circuit 250.

When a radiation image of the object 8 is recorded, the object 8 is placed at the position shown in FIG. 10, and the motors 235 and 245 are then operated. In this manner, the first slit belt 201, most part of which has been wound around the wind-up shaft 234, is wound up around the wind-up shaft 233. Also, the second slit belt 202, most part of which has been wound around the wind-up shaft 244, is wound up around the wind-up shaft 243. Therefore, the part of the first slit belt 201, which has been positioned between the wind-up shaft 233 and the wind-up shaft 234, and the part of the second slit belt 202, which has been positioned between the wind-up shaft 243 and the wind-up shaft 244, are moved leftwardly in FIG. 10. In this state, the radiation source 9 is activated to produce radiation 7 for a predetermined period of time, and the radiation 7 is irradiated to the object 8. The radiation 7 passes through the slit-like gaps 232, 232, . . . on the first slit belt 201. A plurality of streaks of the linear radiation 7, which has passed through the slit-like gaps 232, 232, . . . pass through the object 8. At this time, as indicated by the arrows 7A, 7A, . . . part of the radiation 7 is scattered by the object 8. Most of the scattered radiation 7A is absorbed by the radiation absorbers 241, 241, . . . of the second slit belt 202. Therefore, approximately only the primary radiation (i.e. the direct radiation) impinges upon the stimulable phosphor sheet 10.

Also, at this time, the drive control circuit 250 controls the motors 235 and 245 in accordance with the outputs of the encoders 237 and 247. In this manner, the first slit belt 201 and the second slit belt 202 are moved synchronously such that a plane, which passes through one of the slit-like gaps 232, 232, . . . on the first slit belt 201 and through one of the slit-like gaps 242, 242, . . . on the second slit belt 202, may pass through the radiation source 9. When the first slit belt 201 and the second slit belt 202 are thus moved, the slit-like gaps 232, 232, . . . and the slit-like gaps 242, 242, . . . also move, and the object 8 is scanned with the linear radiation 7. In this manner, a radiation image of the object 8 is stored with the linear radiation 7 on the stimulable phosphor sheet 10.

When the operation for recording the radiation image is finished, the motors 238 and 239 are operated. In this manner, most part of the first slit belt 201 is wound around the wind-up shaft 234. Also, most part of the second slit belt 202 is wound around the wind-up shaft 244. Therefore, the next operation for recording a radiation image can then be carried out.

As described above, most of the scattered radiation 7A is absorbed by the radiation absorbers 241, 241, . . . of the second slit belt 202. Therefore, the radiation image stored on the stimulable phosphor sheet 10 is not adversely affected by the scattered radiation 7A and has good image quality free of any noise.

Also by quickly rotating the wind-up shaft 233 and the wind-up shaft 243, the flexible first slit belt 201 and the flexible second slit belt 202 can be rotated quickly. Therefore, the stimulable phosphor sheet 10 can be scanned quickly with the linear radiation 7. Accordingly, with this embodiment of the third radiation image recording apparatus in accordance with the present invention, the time required for a radiation image to be recorded can be kept short, and the image recording capacity can be kept high. Also, with this embodiment, little artifact is caused to occur by movement of the object 8 during the slit exposure operation.

Additionally, with this embodiment, the first slit belt 201 is moved a distance longer than the intervals between the slit-like gaps 232, 232, . . . while the radiation is being produced by the radiation source. (By way of example, the first slit belt 201 is moved a distance as long as at least two times the intervals between the slit-like gaps 232, 232, . . . The first slit belt 201 should preferably be moved a distance as long as at least five times the intervals between the slit-like gaps 232, 232, . . .) Also, the second slit belt 202 is moved a distance longer than the intervals between the slit-like gaps 242, 242, . . . while the radiation is being produced by the radiation source. (By way of example, the second slit belt 202 is moved a distance as long as at least two times the intervals between the slit-like gaps 242, 242, . . . The second slit belt 202 should preferably be moved a distance as long as at least five times the intervals between the slit-like gaps 242, 242, . . .) In such cases, a single part of the stimulable phosphor sheet 10 is scanned several times with the linear radiation 7, and a radiation image is thereby recorded on the stimulable phosphor sheet 10. Therefore, in the recorded radiation image, no perceptible artifact occurs at boundaries between regions scanned different times with the linear radiation 7.

The radiation image, which has been stored on the stimulable phosphor sheet 10, is read out in the same manner as that described above with reference to FIG. 3, and the read-out image signal thus obtained is used in reproducing a visible image.

Figure 12:
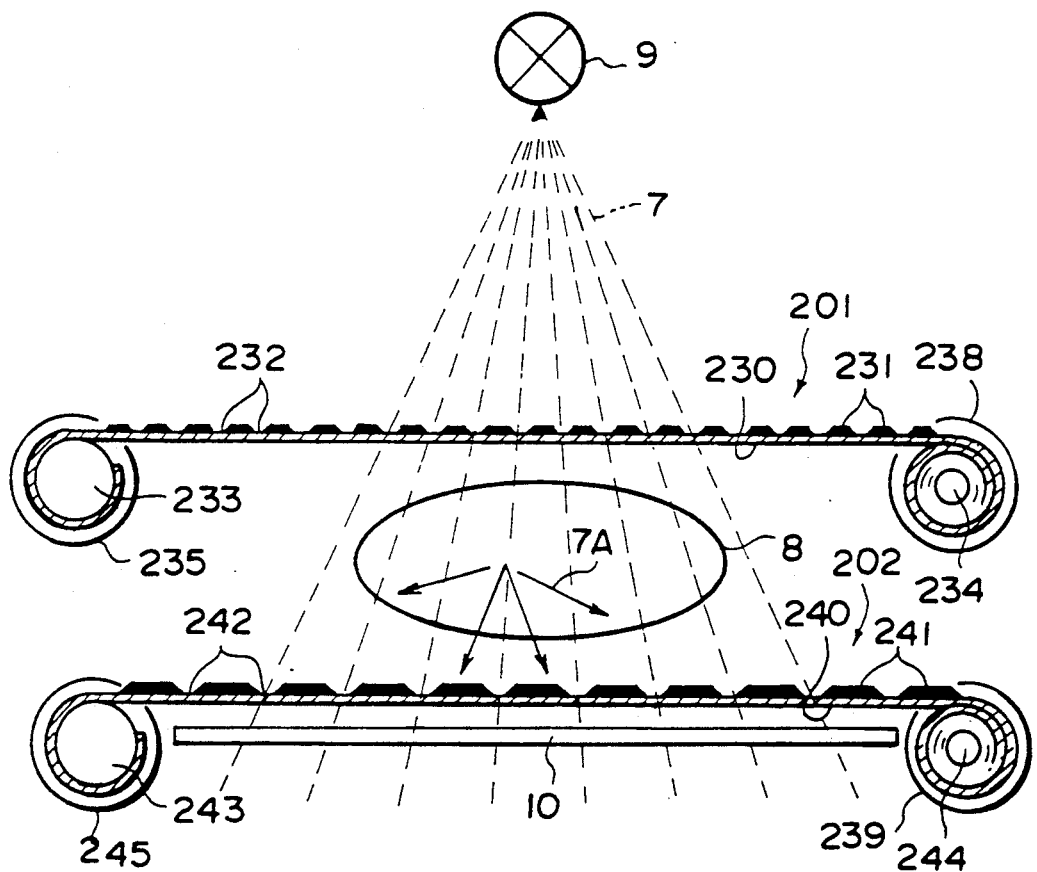
FIG. 12 is a partially cutaway front view showing a different embodiment of the third radiation image recording apparatus in accordance with the present invention.
Figure 13:
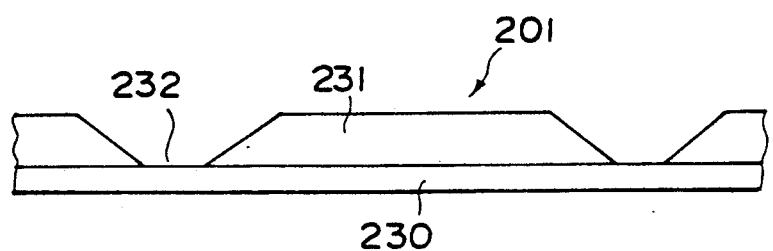
FIG. 13 is an enlarged front view showing the major part of the embodiment of FIG. 12, and FIGS. 14A and 14B represent partially cutaway front views showing different embodiments of the third radiation image recording apparatus in accordance with the present invention.

A different embodiment of the third radiation image recording apparatus in accordance with the present invention will be described hereinbelow with reference to FIGS. 12 and 13. In FIGS. 12 and 13, similar elements are numbered with the same reference numerals with respect to FIG. 10. (This also applies to the drawing that follows.)

As illustrated in FIG. 13, each of the radiation absorbers 231, 231, . . . of the first slit belt 201 has a cross-sectional shape such that both ends of the radiation absorber 231, which ends are taken in the direction along which the radiation absorbers 231, 231, . . . stand side by side with each other, may become progressively thinner towards the adjacent slit-like gaps 232, 232. The radiation absorbers 241, 241, . . . of the second slit belt 202 have the same cross-sectional shapes as those of the radiation absorbers 231, 231, . . . Therefore, in the recorded radiation image, less artifact occurs at boundaries between regions scanned different times with the linear radiation 7. In FIG. 12, the mechanism for synchronously moving the first slit belt 201 and the second slit belt 202 is not shown. As this mechanism, by way of example, the mechanism shown in FIG. 10 may be employed.

A further embodiment of the third radiation image recording apparatus in accordance with the present invention will be described hereinbelow with reference to FIG. 14A. In this embodiment, an endless belt is employed as a second slit belt 203. The second slit belt 203 is threaded over a driving drum 253 and a driven drum 254 and located such that one of the parts positioned between the driving drum 253 and the driven drum 254 may intervene between the object 8 and the stimulable phosphor sheet 10. The driving drum 253 is rotated by the motor 245, which is of the same type as the motor 245 shown in FIG. 10, and the second slit belt 203 is thereby moved.

Figure 14A:
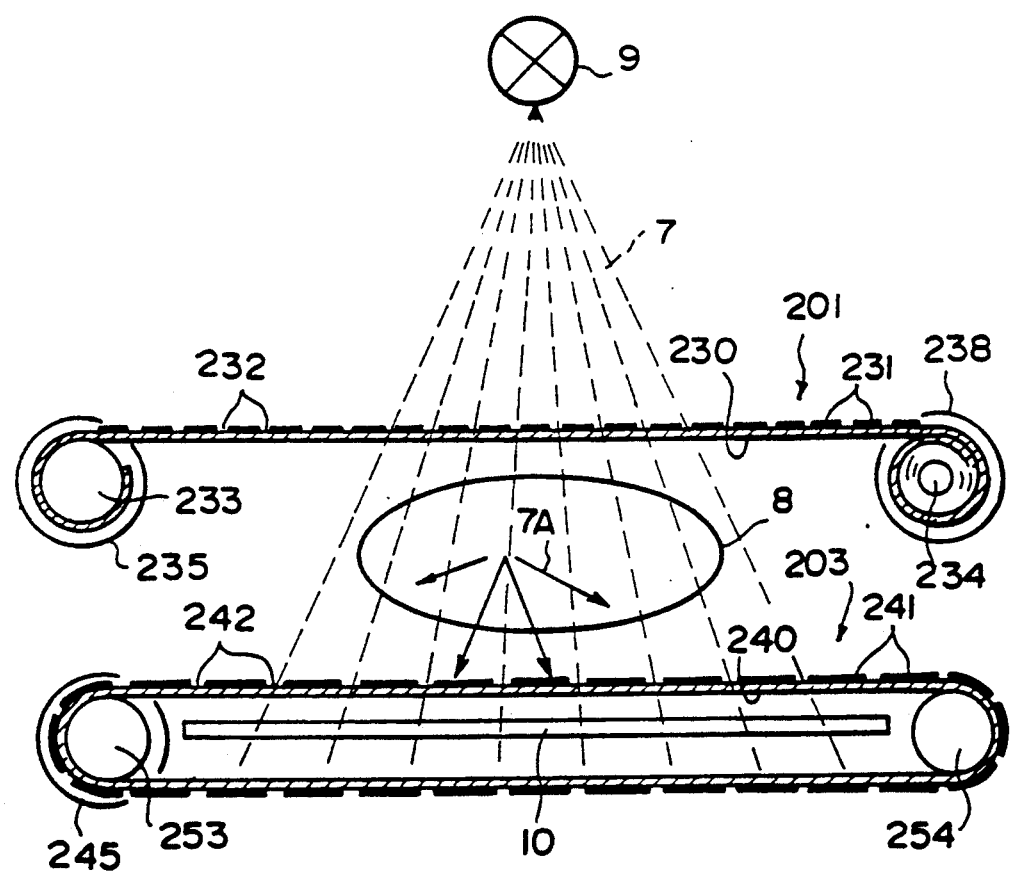

With the embodiment of FIG. 14A, the second slit belt 203 may be moved in only one direction, and no means is necessary to move the second slit belt 203 in the reverse direction. Therefore, the cost of the radiation image recording apparatus can be kept low.

Figure 14B:
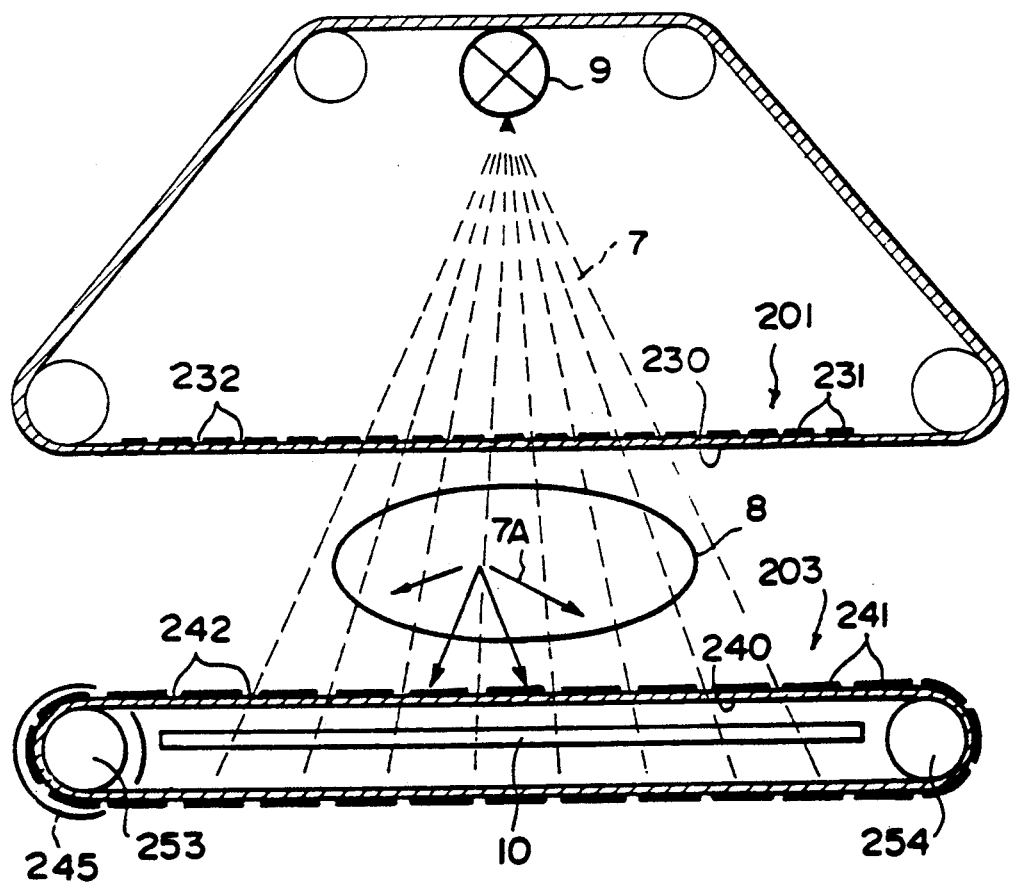

Alternatively, both the first slit belt 201 and the second slit belt 203 may be constituted of endless belts, as illustrated in FIG. 14B, and the radiation source 9 may be located inside of the space defined by the endless first slit belt 201.

In the embodiments of FIGS. 10, 12, and 14, the speed, with which the first slit belt 201, the second slit belt 202, or the second slit belt 203 moves, is detected from the radiation absorbers 231, 231, . . . or the radiation absorbers 241, 241, . . . which stand side by side with each other. Alternatively, optical grids, magnetic grids, or the like, may be located at a side end of the long strip-shaped radiation-permeable substrate 230 or the radiation-permeable substrate 240 such that they may stand side by side in the longitudinal direction of the long strip-shaped radiation-permeable substrate 230 or the radiation-permeable substrate 240. The speed, with which the first slit belt 201, the second slit belt 202, or the second slit belt 203 moves, may then be detected from the optical grids, the magnetic grids, or the like.

What is claimed is:

1. A radiation image recording apparatus which comprises:

i) a radiation source for producing radiation, ii) a radiation image recording medium, which is located facing said radiation source, iii) a first slit plate composed of a radiation absorber and at least two slits, which are formed parallel to each other and through which said radiation passes, said first slit plate being located between said radiation source and an object plane, wherein in use an object is placed in said object plane between said radiation source and said radiation image recording medium, iv) a second slit plate composed of a radiation absorber and at least two slits, which are formed parallel to each other and through which said radiation passes, said second slit plate being located between said object plane and said radiation image recording medium such that at least two said slits of said second slit plate are parallel to at least two said slits of said first slit plate, and v) a drive means for synchronously moving said first slit plate and said second slit plate in the direction, along which said slits stand side by side with each other, such that a plane, which passes through one of at least two said slits of said first slit plate and one of at least two said slits of said second slit plate, passes through said radiation source, wherein at least one of said first slit plate and said second slit plate has a cross-sectional shape such that the thicknesses of walls, which extend on both sides of each slit and define each said slit, becomes progressively smaller towards each said slit.

2. An apparatus as defined in claim 1 wherein at least one of said first slit plate and said second slit plate is composed of a plate-like radiation absorber and slits, which are formed through said plate-like radiation absorber.

3. An apparatus as defined in claim 1 wherein at least one of said first slit plate and said second slit plate is composed of a plate-like, radiation-permeable material and a plurality of radiation absorbers, which are located side by side with each other on said plate-like, radiation-permeable material such that slit-like gaps may intervene between the plurality of said radiation absorbers.

4. An apparatus as defined in claim 1, 2, or 3 wherein both said first slit plate and said second slit plate have a cross-sectional shape such that the thicknesses of walls, which extend on both sides of each said slit and define each said slit, becomes progressively smaller towards each said slit.

5. An apparatus as defined in claim 1, 2, or 3 wherein only one of said first slit plate and said second slit plate has a cross-sectional shape such that the thicknesses of walls, which extend on both sides of each said slit and define each said slit, becomes progressively smaller towards each said slit.

6. An apparatus as defined in claim 1, 2, or 3 wherein the widths of said slits and the intervals between said slits of said first slit plate and the widths of said slits and the intervals between said slits of said second slit plate are set such that they are proportional to the distances from said radiation source.

7. An apparatus as defined in claim 1, 2, or 3 wherein said first slit plate and said second slit plate are constituted of lead.

8. An apparatus as defined in claim 1, 2, or 3 wherein said radiation image recording medium is a stimulable phosphor sheet.

9. The apparatus as defined in claim 1 wherein at least one of said first slit plate and said second slit plate is composed of a strip-shaped, radiation-permeable material, and a plurality of radiation absorbers, which are located side by side with each other on said strip-shaped, radiation-permeable material such that slit-like gaps intervenes between the plurality of said radiation absorbers.

10. A radiation image recording apparatus which comprises:

i) a radiation source for producing radiation, ii) a radiation image recording medium, which is located facing said radiation source, iii) a first group of a plurality of cylindrical radiation absorbers, which are located between said radiation source and an object plane, wherein in use an which object is placed in said object plane between said radiation source and said radiation image recording medium, such that the first group of the plurality of said cylindrical radiation absorbers stand side by side with each other with gaps intervening therebetween, each of the first group of the plurality of said cylindrical radiation absorbers being supported such that each cylindrical radiation absorber can rotate around an eccentric shaft, which is shifted from a center axis of each said cylindrical radiation absorber, iv) a second group of a plurality of cylindrical radiation absorbers, which are located between said object plane and said radiation image recording medium such that the second group of the plurality of said cylindrical radiation absorbers may stand side by side with each other with gaps intervening therebetween, each of the second group of the plurality of said cylindrical radiation absorbers being supported such that each said cylindrical radiation absorber can rotate around an eccentric shaft, which is shifted from a center axis of each said cylindrical radiation absorber, and v) a drive means for synchronously rotating the first group of the plurality of said cylindrical radiation absorbers and the second group of the plurality of said cylindrical radiation absorbers such that a plane, which passes through one of the gaps intervening between the first group of the plurality of said cylindrical radiation absorbers and through one of the gaps intervening between the second group of the plurality of said cylindrical radiation absorbers, passes through said radiation source.

11. An apparatus as defined in claim 10 wherein the first group of the plurality of said cylindrical radiation absorbers stand side by side with each other along a straight line, the second group of the plurality of said cylindrical radiation absorbers stand side by side with each other along a straight line, and said radiation image recording medium is located parallel to the direction, along which the first group of the plurality of said cylindrical radiation absorbers or the second group of the plurality of said cylindrical radiation absorbers stand side by side with each other.

12. An apparatus as defined in claim 11 wherein the first group of the plurality of said cylindrical radiation absorbers are located such that the widths of the gaps formed between the cylindrical radiation absorbers, which are located at the ends of the array of the first group of the plurality of said cylindrical radiation absorbers, and the widths of the gaps formed between the cylindrical radiation absorbers, which are located at the middle of the array of the first group of the plurality of said cylindrical radiation absorbers, and the second group of the plurality of said cylindrical radiation absorbers are located such that the widths of the gaps formed between the cylindrical radiation absorbers, which are located at the ends of the array of the second group of the plurality of said cylindrical radiation absorbers, and the widths of the gaps formed between the cylindrical radiation absorbers, which are located at the middle of the array of the second group of the plurality of said cylindrical radiation absorbers, whereby the solid angles of a plurality of streaks of the linear radiation passing through the gaps are made uniform.

13. An apparatus as defined in claim 10 wherein the first group of the plurality of said cylindrical radiation absorbers, the second group of the plurality of said cylindrical radiation absorbers, and said radiation image recording medium are located along arcs of three concentric circles having their centers at a focal point of said radiation source.

14. An apparatus as defined in claim 10, 11, 12, or 13 wherein the first group of the plurality of said cylindrical radiation absorbers and the second group of the plurality of said cylindrical radiation absorbers have a true circular cross-sectional shape.

15. An apparatus as defined in claim 10, 11, 12, or 13 wherein the first group of the plurality of said cylindrical radiation absorbers and the second group of the plurality of said cylindrical radiation absorbers have an elliptic cross-sectional shape such that the speeds, with which the small gaps move as the first group of the plurality of said cylindrical radiation absorbers and the second group of the plurality of said cylindrical radiation absorbers rotate, are made uniform.

16. An apparatus as defined in claim 10, 11, 12, or 13 wherein a counter weight is secured to said eccentric shaft, which supports each of the first group of the plurality of said cylindrical radiation absorbers, said counter weight being located on the side opposite to each said cylindrical radiation absorber with respect to said eccentric shaft, and/or a counter weight is secured to said eccentric shaft, which supports each of the second group of the plurality of said cylindrical radiation absorbers, said counter weight being located on the side opposite to each said cylindrical radiation absorber with respect to said eccentric shaft.

17. An apparatus as defined in claim 10, 11, 12, or 13 wherein the first group of the plurality of said cylindrical radiation absorbers and/or the second group of the plurality of said cylindrical radiation absorbers are constituted of lead.

18. An apparatus as defined in claim 10, 11, 12, or 13 wherein said radiation image recording medium is a stimulable phosphor sheet.

19. A radiation image recording apparatus comprising:

i) a radiation source for producing radiation, ii) a radiation image recording medium, which is located facing said radiation source, iii) a first slit belt composed of a flexible, strip-shaped, radiation-permeable substrate and a plurality of radiation absorbers, which are supported on said radiation-permeable substrate such that slit-like gaps intervenes between the plurality of said radiation absorbers, said first slit belt being located between said radiation source and an object plane, where in use an object is placed in said object plane between said radiation source and said radiation image recording medium, iv) a second slit belt composed of a flexible, strip-shaped, radiation-permeable substrate and a plurality of radiation absorbers, which are supported on said radiation-permeable substrate such that slit-like gaps intervenes between the plurality of said radiation absorbers, said second slit belt being located between said object plane and said radiation image recording medium such that said slit-like gaps on said second slit belt are parallel to said slit-like gaps on said first slit belt, where each of said radiation absorbers of at least one of said first slit belt and said second slit belt has a cross-sectional shape such that both ends of each said radiation absorber, which ends are in a direction along which said radiation absorbers stand side by side with each other, becomes progressively thinner towards the adjacent slit-like gaps, v) a first belt moving means provided with rotatable members, which are engaged with said first slit belt and move said first slit belt in the direction, which is normal to the direction along which each slit-like gap on said first slit belt extends, vi) a second belt moving means provided with rotatable members, which are engaged with said second slit belt and move said second slit belt in the direction, which is normal to the direction along which each said slit-like gap on said second slit belt extends, and vii) a control means for controlling said first belt moving means and said second belt moving means and synchronously moving said first slit belt and said second slit belt such that a plane, which passes through one of said slit-like gaps on said first slit belt and through one of said slit-like gaps on said second slit belt, passes through said radiation source.

20. An apparatus as defined in claim 19 wherein at least one of said first slit belt and said second slit belt is constituted of a belt having ends, which are engaged with said rotatable members of said first belt moving means and said second belt moving means, respectively.

21. An apparatus as defined in claim 19 wherein at least one of said first slit belt and said second slit belt is constituted of an endless belt.

22. An apparatus as defined in claim 19, 20, or 21 wherein said radiation absorbers of at least one of said first slit belt and said second slit belt are constituted of a composition containing a polymer and a heavy metal.

23. An apparatus as defined in claim 19, 20, or 21 wherein said first slit belt is moved a distance as long as at least two times the intervals between said slit-like gaps on said first slit belt while said radiation source is producing the radiation, and said second slit belt is moved a distance as long as at least two times the intervals between said slit-like gaps on said second slit belt while said radiation source is producing the radiation.

24. An apparatus as defined in claim 19, 20, or 21 wherein said radiation image recording medium is a stimulable phosphor sheet.

25. An apparatus as defined in claim 19, 20, or 21 wherein said radiation absorbers of at least one of said first slit belt and said second slit belt are constituted of a composition containing a heavy element compound dispersed in said polymer.

* * * * *